US010251894B2

(12) United States Patent
Rogawski et al.

(10) Patent No.: US 10,251,894 B2
(45) Date of Patent: Apr. 9, 2019

(54) ANTICONVULSANT ACTIVITY OF STEROIDS

(71) Applicant: The Regents of the University of California, Oakland, CA (US)

(72) Inventors: Michael A. Rogawski, Sacramento, CA (US); Dorota Zolkowska, Davis, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 15/917,245

(22) Filed: Mar. 9, 2018

(65) Prior Publication Data

US 2018/0193357 A1 Jul. 12, 2018

Related U.S. Application Data

(60) Division of application No. 15/632,360, filed on Jun. 25, 2017, now abandoned, which is a continuation of application No. 14/646,886, filed as application No. PCT/US2013/072351 on Nov. 27, 2013, now abandoned.

(60) Provisional application No. 61/732,252, filed on Nov. 30, 2012.

(51) Int. Cl.
*A61K 31/57* (2006.01)
*A61K 47/40* (2006.01)
*A61K 31/56* (2006.01)
*A61K 9/00* (2006.01)
*A61K 9/08* (2006.01)
*A61K 31/573* (2006.01)

(52) U.S. Cl.
CPC ............ *A61K 31/57* (2013.01); *A61K 9/0019* (2013.01); *A61K 9/08* (2013.01); *A61K 31/56* (2013.01); *A61K 31/573* (2013.01); *A61K 47/40* (2013.01)

(58) Field of Classification Search
CPC ........ A61K 31/57; A61K 31/573; A61K 9/08; A61K 9/0019; A61K 47/40; A61K 31/56
See application file for complete search history.

(56) References Cited

U.S. PATENT DOCUMENTS

| | | | |
|---|---|---|---|
| 3,865,939 A | 2/1975 | Jandacek | |
| 5,719,197 A | 2/1998 | Kanios et al. | |
| 6,245,757 B1 | 6/2001 | Chopp et al. | |
| 6,455,516 B1 | 9/2002 | Backstrom et al. | |
| 6,780,853 B1 | 8/2004 | Upasani et al. | |
| 7,060,255 B2 | 6/2006 | Rabinowitz et al. | |
| 7,064,116 B2 | 6/2006 | Calogeropoulou et al. | |
| 7,090,830 B2 | 8/2006 | Hale et al. | |
| 7,630,757 B2 | 12/2009 | Dorfmeister et al. | |
| 7,816,074 B2 | 10/2010 | Smith et al. | |
| 7,858,609 B2 | 12/2010 | Shaw et al. | |
| 8,012,958 B2 | 9/2011 | Sabnani et al. | |
| 8,697,678 B2 | 4/2014 | Goodchild et al. | |
| 8,969,329 B2 | 3/2015 | Brinton et al. | |
| 9,084,797 B2 | 7/2015 | Caufriez et al. | |
| 2002/0072509 A1 | 6/2002 | Stein et al. | |
| 2003/0032638 A1 | 2/2003 | Kim et al. | |
| 2006/0063707 A1 | 3/2006 | Baudry et al. | |
| 2006/0198896 A1 | 9/2006 | Liversidge et al. | |
| 2007/0081948 A1 | 4/2007 | Morton | |
| 2007/0287931 A1 | 12/2007 | Dilorenzo | |
| 2008/0195160 A1 | 8/2008 | Wingeier et al. | |
| 2008/0269183 A1 | 10/2008 | Mellon et al. | |
| 2009/0074677 A1 | 3/2009 | Marx et al. | |
| 2009/0130216 A1 | 5/2009 | Cartt et al. | |
| 2009/0162441 A1 | 6/2009 | Bartus et al. | |
| 2009/0198145 A1 | 8/2009 | Chow | |
| 2009/0203658 A1 | 8/2009 | Marx et al. | |
| 2009/0221544 A1 | 9/2009 | Stein et al. | |
| 2009/0239942 A1 | 9/2009 | Cloyd | |
| 2009/0325920 A1 | 12/2009 | Hoffman et al. | |
| 2010/0136105 A1 | 6/2010 | Chen et al. | |
| 2010/0234335 A1 | 9/2010 | Gravanis et al. | |
| 2010/0297181 A1 | 11/2010 | Hanada et al. | |
| 2010/0316678 A1 | 12/2010 | Goodchild | |
| 2010/0331762 A1 | 12/2010 | Wingeier et al. | |
| 2011/0054038 A1 | 3/2011 | Glozman | |
| 2011/0152840 A1 | 6/2011 | Lee et al. | |
| 2011/0288059 A1 | 11/2011 | Marx et al. | |
| 2011/0306579 A1 | 12/2011 | Stein | |
| 2011/0319386 A1 | 12/2011 | Barlow et al. | |
| 2012/0142645 A1 | 6/2012 | Marx | |
| 2012/0302535 A1 | 11/2012 | Caufriez et al. | |
| 2013/0210783 A1 | 8/2013 | Marx et al. | |
| 2013/0309306 A1 | 11/2013 | Rogawski et al. | |
| 2014/0050789 A1 | 2/2014 | Rogawski et al. | |

(Continued)

FOREIGN PATENT DOCUMENTS

CA 2 443 466 A1 12/2002
EP 0 233 849 A1 1/1987

(Continued)

OTHER PUBLICATIONS

Gilbert et al, Gynecol Endocrinol. 21(5):268-79. (Year: 2005).*
Kaura et al, European Neuropsychopharmacology, 17, 108-115 (Year: 2007).*
PCT International Search Report and Written Opinion dated Dec. 27, 2012 issued in PCT/US2012/056509.
PCT International Search Report and Written Opinion dated Mar. 17, 2014 issued in PCT/US2013/072351.

(Continued)

*Primary Examiner* — Sudhakar Katakam
(74) *Attorney, Agent, or Firm* — Squire Patton Boggs (US) LLP

(57) ABSTRACT

The present invention relates to methods of preventing, inhibiting, delaying, and/or mitigating seizures by administration of a steroid, e.g., a neurosteroid, e.g., allopregnanolone.

3 Claims, 10 Drawing Sheets

(56) References Cited

U.S. PATENT DOCUMENTS

| | | |
|---|---|---|
| 2014/0057885 A1 | 2/2014 | Reddy et al. |
| 2014/0148412 A1 | 5/2014 | Hogenkamp |
| 2014/0322198 A1 | 10/2014 | Buchwald-Werner et al. |
| 2014/0343027 A1 | 11/2014 | Rogawski et al. |
| 2015/0018327 A1 | 1/2015 | Reddy |
| 2015/0158903 A1 | 6/2015 | Upasani et al. |
| 2015/0175651 A1 | 6/2015 | Salituro et al. |
| 2015/0265632 A1 | 9/2015 | Goodchild et al. |
| 2015/0290181 A1 | 10/2015 | Lee et al. |
| 2015/0313915 A1 | 11/2015 | Rogawski et al. |
| 2018/0050005 A1 | 2/2018 | DiMauro et al. |
| 2018/0050107 A1 | 2/2018 | DiMauro et al. |
| 2018/0064728 A1 | 3/2018 | Chang et al. |
| 2018/0071315 A1 | 3/2018 | Cashman et al. |
| 2018/0133229 A1 | 5/2018 | Rogawski et al. |
| 2018/0153906 A1 | 6/2018 | Rogawski et al. |
| 2018/0193357 A1 | 7/2018 | Rogawski et al. |
| 2018/0235916 A1 | 8/2018 | Kaufman et al. |
| 2018/0256726 A1 | 9/2018 | Rogawski et al. |

FOREIGN PATENT DOCUMENTS

| | | |
|---|---|---|
| EP | 0 808 325 A1 | 11/1997 |
| JP | 2009-524582 A | 7/2009 |
| JP | 2015-513316 A | 5/2015 |
| WO | WO 91/11172 A1 | 8/1991 |
| WO | WO 91/016897 | 11/1991 |
| WO | WO 93/03732 A1 | 3/1993 |
| WO | WO 95/21617 A1 | 8/1995 |
| WO | WO 96/16076 A1 | 5/1996 |
| WO | WO 97/03677 A1 | 2/1997 |
| WO | WO 99/45931 A1 | 9/1999 |
| WO | WO 02/30409 A2 | 4/2002 |
| WO | WO 2004/019953 A1 | 3/2004 |
| WO | WO 2006/102644 A2 | 9/2006 |
| WO | WO 2007/062266 A2 | 5/2007 |
| WO | WO 2008/157460 A1 | 12/2008 |
| WO | WO 2010/042925 A2 | 4/2010 |
| WO | WO 2010/063030 A2 | 6/2010 |
| WO | WO 2010/107815 A1 | 9/2010 |
| WO | WO 2011/088503 A1 | 7/2011 |
| WO | WO 2012/059456 A1 | 5/2012 |
| WO | WO 2012/075286 A2 | 6/2012 |
| WO | WO 2013/036835 | 3/2013 |
| WO | WO 2013/043985 A1 | 3/2013 |
| WO | WO 2013/056181 | 4/2013 |
| WO | WO 2013/112605 | 8/2013 |
| WO | WO 2013/188792 | 12/2013 |
| WO | WO 2014/028398 A2 | 2/2014 |
| WO | WO 2014/031792 A2 | 2/2014 |
| WO | WO 2014/085668 A1 | 6/2014 |
| WO | WO 2014/108808 A2 | 7/2014 |
| WO | WO 2015/195962 | 12/2015 |
| WO | WO 2017/156103 | 9/2017 |

OTHER PUBLICATIONS

Akhondzadeh, et al., "Induction of a novel form of hippocampal longterm depression by muscimol: involvement of $GABA_A$ but not glutamate receptors" *British Journal of Phamacology* 115:527-533, 1995.

Amin, et al., "The interaction of neuroactive steroids and GABA in the development of neuropsychiatric disorders in women" *Pharmacology, Biochemistry and Behavior* 84:635-643, 2006.

Baker, et al., "Reproductive Endocrinology: Efficacy of Progesterone Vaginal Suppositories in Alleviation of Nervous Symptoms in Patients with Premenstrual Syndrome" *Journal of Assisted Reproduction and Genetics* 12(3):205-209, 1995.

Bali et al. "Multifunctional aspects of allopregnanolone in stress and related disorders," *Progress in Neuro-Psychopharmacology & Biological Psychiatry*, 48:64-78, 2014.

Bernardi, et al., "Disadaptive disorders in women: allopregnanolone, a sensitive steroid" *Gynecol Endocrinol* 19:344-353, 2004.

Bičíková, et al., "Serum Concentrations of Some Neuroactive Steroids in Women Suffering from Mixed Anxiety-Depressive Disorder" *Neurochemical Research* 25(12):1623-1627, 2000.

Birzniece, et al., "Neuroactive steroid effects on cognitive functions with a focus on the serotonin and GABA systems" *Brain Research Review* 51:212-239, 2006.

Bäckström, et al., "Pathogenesis in Menstrual Cycle-Linked CNS Disorders" *Annals New York Academy of Sciences* 1007:42-53, 2003.

Carta et al. " GABAergic neuroactive steroids: a new frontier in bipolar disorders?," *Behavioral and Brain Functions*, 8:61, 8pp, 2012.

D'Aquila et al. "Dopamine is involved in the antidepressant-like effect of allopregnanolone in the forced swimming test in female rats," *Behavioural Pharmacology*, 21:21-28, 2010.

Deligiannidis et al. "GABAergic neuroactive steroids and resting-state functional connectivity in postpartum depression: a preliminary study," *Journal of Psychiatric Research*, 47:816-828, 2013.

Drugan, et al., "Resilience in shock and swim stress models of depression" *Frontiers in Behavioral Neuroscience* 7(14):1-8, 2013.

Eser et al. (2006) "Neuroactive Steroids in Depression and Anxiety Disorders: Clinical Studies," *Neuroendocrinology*, 84:244-254.

Eser et al. (2006) "Neuropsychopharmacological properties of neuroactive steroids in depression and anxiety disorders" *Psychopharmacology*, 186:373-387.

Evans et al. "Allopregnanolone regulates neurogenesis and depressive/anxiety-like behaviour in a social isolation rodent model of chronic stress," *Neuropharmacology*, 63:1315-1326, 2012.

Freeman, et al., "Allopregnanolone Levels and Symptom Improvement in Severe Premenstrual Syndrome" *J Clin Psychopharmacol.* 22(5):516-520, 2002.

Frye et al., "Effects and mechanisms of 3α, 5α,-THP on emotion, motivation, and reward functions involving pregnane xenobiotic receptor," *Frontiers in Neuroscience*, 5(136): 18pp, 2012.

Frye, et al., "Changes in Progesterone Metabolites in the Hippocampus Can Modulate Open Field and Forced Swim Test Behavior of Proestrous Rats" *Hormones and Behavior* 41:306-315, 2002.

Frye, et al., "Hippocampal 3α,5α-THP may alter depressive behavior of pregnant and lactating rats" *Pharmacology, Biochemistry and Behavior* 78:531-540, 2004.

Girdler, et al., "Neurosteroids in the context of stress: Implications for depressive disorders" *Pharmacology & Therapeutics* 116:125-139, 2007.

Griffin, et al., "Current Perspectives on the Role of Neurosteroids in PMS and Depression" *International Review of Neurobiology* 46:479-492, 2001.

Guidotti, et al., "The socially-isolated mouse: a model to study the putative role of allopregnanolone and 5α-dihydroprogesterone in psychiatric disorders" *Brain Research Reviews* 37:110-115, 2001.

Hardoy, et al., "Increased Neuroactive Steroid Concentrations in Women With Bipolar Disorder or Major Depressive Disorder" *Journal of Clinical Psychopharmacology* 26(4):379-384, 2006.

Hardoy, et al., "The link between neurosteroids and syndromic/syndromal components of the mood spectrum disorders in women during the premenstrualq phase" *Clinical Practice and Epidemiology in Mental Health* 4(3):1-8, 2008.

Huber, et al., "Effect of an Oral Contraceptive with Chlormadinone Acetate on Depressive Mood" *Clin Drug Invest* 28(12):783-791, 2008.

Khisti, et al., "Serotonergic agents modulate antidepressant-like effect of the neurosteroid 3α-hydroxy-5α-pregnan-20-one in mice" *Brain Research* 865:291-300, 2000.

Klatzkin, et al., "Associations of histories of depression and PMDD diagnosis with allopregnanolone concentrations following the oral administration of micronized progesterone" *Psychoneuroendocrinology* 31:1208-1219, 2006.

Klatzkin, et al., "Histories of depression, allopregnanolone responses to stress, and premenstrual symptoms in women" *Biological Psychology* 71:2-11, 2006.

Mackenzie, et al., "Neurosteroids and Gabaergic Signaling in Health and Disease" *Biomol Concepts* 4(1):29-42, 2013.

(56) References Cited

OTHER PUBLICATIONS

Marx, et al., "Neuroactive Steroids are Altered in Schizophrenia and Bipolar Disorder: Relevance to Pathophysiology and Therapeutics" *Neuropsychopharmacology* 31:1249-1263, 2006.
Matsumoto, et al. ,"$GABA_A$ receptor neurotransmission dysfunction in a mouse model of social isolation-induced stress: Possible insights into a non-serotonergic mechanism of action of SSRIs in mood and anxiety disorders" Stress 10(1):3-12, 2007.
Morgan, et al., "Neuroactive steroids after estrogen exposure in depressed postmenopausal women treated with sertraline and asymptomatic postmenopausal women" *Arch Womens Ment Health* 13:91-98, 2010.
Murayama, et al., "Effects of neurosteroid 3α-hydroxy-5α-pregnan-20-one on ethanol-mediated paired-pulse depression of population spikes in the CA1 region of rat hippocampal slices" *Neuroscience Letters* 394:28-32, 2006.
Naert, et al., "Neuroactive steroids modulate HPA axis activity and cerebral brain-derived neurotrophic factor (BDNF) protein levels in adult male rats" Psychoneuroendocrinology 32:1062-1078, 2007.
Nappi et al., "Serum Allopregnanolone in Women With Postpartum "Blues"," *Obstetrics & Gynecology* 97(1):77-80, 2001.
Nin, et al., "Neurosteroids reduce social isolation-induced behavioral deficits: a proposed link with neurosteroid-mediated upregulation of BDNF expression" *Frontiers in Endocrinology* 2(73):1-12, 2011.
Pearlstein, et al., "Premenstrual Dysphoric Disorder: Burden of Illness and Treatment Update" *J Psychiatry Neurosci* 33(4):291-301, 2008.
Pinna, et al., "Up-Regulation of Neurosteroid Biosynthesis as a Pharmacological Strategy to Improve Behavioural Deficits in a Putative Mouse Model of Post-Traumatic Stress Disorder" *Journal of Neuroendocrinology* 24:102-116, 2011.
Puia et al. "Novel modulatory effects of neurosteroids and benzodiazepines on excitatory and inhibitory neurons excitability: a multi-electrode array recording study," *Frontiers in Neural Circuits*, 6(94):17pp, Nov. 2012.
Rapkin, et al., "Progesterone Metabolite Allopregnanolone in Women with Premenstrual Syndrome" *Obstetrics & Gynecology* 90(5):709-714, 1997.
Rasmusson, et al., "Decreased Cerebrospinal Fluid Allopregnanolone Levels in Women with Posttraumatic Stress Disorder" *Biol Psychiatry* 60:704-713, 2006.
Reddy, Doodipala S., "The Clinical Potentials of Endogenous Neurosteroids" *Drugs of Today* 38(7):465-485, 2002.
Reddy, Doodipala Samba, "Neurosteroids: Endogenous role in the human brain and therapeutic potentials" Progress in Brain Research 186(8):113-137, 2010.
Reddy, Doodipala Samba, "Pharmacology of Endogenous Neuroactive Steroids" *Critical Reviews™ in Neurobiology* 15(3&4):197-234, 2003.
Romeo, et al., "Effects of Antidepressant Treatment on Neuroactive Steroids in Major Depression" *Am J Psychiatry* 155(7):910-913, 1998.
Rougé-Pont, et al., "Short Communication: The neurosteroid allopregnanolone increases dopamine release and dopaminergic response to morphine in the rat nucleus accumbens" *European Journal of Neuroscience* 16:169-173, 2002.
Rupprecht, et al., "Neuroactive steroids: mechanisms of action and neuropsychopharmacological perspectives" *Trends Neurosci.* 22:410-416, 1999.
Saalmann, et al., "Neurosteroids Involved in Regulating Inhibition in the Inferior Colliculas" *J Neurophysiol* 96:3064-3073, 2006.
Schüle et al. (2011) "Neuroactive Steroids in Affective Disorders: Target for Novel Antidepressant or Anxiolytic Drugs?," *Neuroscience*, 191:55-77.
Sundström Poromaa, et al., "GABA receptors, progesterone and premenstrual dysphoric disorder" *Arch Womens Ment Health* 6:23-41, 2003.
Ungard, et al., "Modification of behavioral effects of drugs in mice by neuroactive steroids" *Psychopharmacology* 148:336-343, 2000.
Uzunova, et al., "Region-specific dysregulation of allopregnanolone brain content in the olfactory bulbectomized rat model of depression" *Brain Research* 976:1-8, 2003.
Uzunova, et al., "Relevance of endogenous 3α-reduced neurosteroids to depression and antidepressant action" *Psychopharmacology* 186:351-361, 2006.
Van Broekhoven, et al., "Neurosteroids in depression: a review" *Psychopharmacology* 165:97-110, 2003.
Wirth, Michelle M., "Beyond the HPA axis: progesterone-derived neuroactive steroids in human stress and emotion" *Frontiers in Endocrinology* 2(19):1-14, 2011.
Wolkowitz, et al., "Depression, disease, and accelerated aging" *Dialogues Clin Neurosci.* 13(1):25-39, 2011.
Zsuzsa, Aszalós, "Neurological and psychiatric aspects of some endocrine diseases. The role of neurosteroids and neuroactive steroids," *Medical Journal* 148(41): 1929-1937, 2007, machine translated into English.
U.S. Restriction Requirement dated Feb. 6, 2015 issued in U.S. Appl. No. 13/972,851.
U.S. Restriction Requirement dated Apr. 6, 2015 issued in U.S. Appl. No. 14/374,080.
U.S. Office Action dated Apr. 16, 2015 issued in U.S. Appl. No. 13/885,660.
U.S. Office Action dated Jun. 12, 2015 issued in U.S. Appl. No. 13/964,922.
U.S. Restriction Requirement dated Aug. 18, 2015 issued in U.S. Appl. No. 14/345,385.
U.S. Restriction Requirement dated Oct. 8, 2015 issued in U.S. Appl. No. 13/972,851.
U.S. Office Action dated Nov. 2, 2015 issued in U.S. Appl. No. 14/374,080.
U.S. Final Office Action dated Nov. 30, 2015 issued in U.S. Appl. No. 13/885,660.
U.S. Office Action dated Feb. 11, 2016 issued in U.S. Appl. No. 14/345,385.
U.S. Restriction Requirement dated Mar. 7, 2016 issued in U.S. Appl. No. 13/972,851.
U.S. Final Office Action dated Apr. 14, 2016 issued in U.S. Appl. No. 13/964,922.
U.S. Restriction Requirement dated May 9, 2016 issued in U.S. Appl. No. 14/646,886.
U.S. Final Office Action dated Jun. 14, 2016 issued in U.S. Appl. No. 14/374,080.
U.S. Office Action dated Jun. 24, 2016 issued in U.S. Appl. No. 13/972,851.
U.S. Final Office Action dated Oct. 31, 2016 issued in U.S. Appl. No. 14/345,385.
U.S. Office Action dated Jan. 4, 2017 issued in U.S. Appl. No. 14/646,886.
U.S. Office Action dated Jan. 19, 2017 issued in U.S. Appl. No. 13/964,922.
U.S. Office Action dated Feb. 22, 2017 issued in U.S. Appl. No. 13/885,660.
U.S. Final Office Action dated Mar. 31, 2017 issued in U.S. Appl. No. 13/972,851.
U.S. Office Action dated Jul. 6, 2017 issued in U.S. Appl. No. 14/345,385.
U.S. Final Office Action dated Oct. 20, 2017 issued in U.S. Appl. No. 13/885,660.
Japanese Office Action dated Jul. 19, 2017 issued in Application No. JP 2015545458.
Australian Examination report No. 1 dated Jul. 27, 2017 issued in Application No. AU 2013352141.
European Examination Report dated Mar. 2, 2017 issued in Application No. EP 13 740 743.3.
European Office Action dated Apr. 5, 2017 issued in Application No. EP 13 85 7993.3.
European Extended Search Report dated May 2, 2016 issued in Application No. EP 13 85 7993.3.
European Extended Search Report dated Jan. 12, 2016 issued in Application No. EP 13 830 765.7.
European Extended Search Report dated Jan. 14, 2016 issued in Application No. EP 13 740 743.3.

(56) References Cited

OTHER PUBLICATIONS

International Search Report (Declaration of non-establishment of International Search Report) and Written Opinion dated Jun. 15, 2012 issued in PCT/US2011/062888.
International Preliminary Report on Patentability and Written Opinion dated Jun. 13, 2013 issued in PCT/US2011/062888.
International Preliminary Report on Patentability and Written Opinion dated Apr. 3, 2014 issued in PCT/US2012/056509.
International Search Report and Written Opinion dated Jan. 13, 2014 issued in PCT/US2013/054562.
International Preliminary Report on Patentability and Written Opinion dated Jun. 18, 2015 issued in PCT/US2013/054562.
International Preliminary Report on Patentability and Written Opinion dated Jun. 11, 2015 issued in PCT/US2013/072351.
International Search Report and Written Opinion dated Mar. 27, 2013 issued in Application No. PCT/US2013/022772.
International Preliminary Report on Patentability and Written Opinion dated Dec. 31, 2014 issued in Application No. PCT/US2013/022772.
International Preliminary Report on Patentability and Written Opinion dated Feb. 24, 2015 issued in Application No. PCT/US2013/056062.
International Search Report and Written Opinion dated Jan. 29, 2014 issued in PCT/US2013/056062.
International Search Report and Written Opinion dated Feb. 5, 2016 issued in PCT/US2015/48937.
International Search Report and Written Opinion dated Aug. 19, 2016 issued in PCT/US2016/026705.
International Search Report and Written Opinion dated Oct. 20, 2016 issued in PCT/US2016/038195.
International Search Report and Written Opinion dated May 22, 2017 issued in PCT/US2017/021325.
"Allopregnanolone for the Treatment of Traumatic Brain Injury," Clinical Trials.gov, [Updated May 22, 2013], pp. 1-4.
"Sage Therapeutics Announces Brexanolone Achieves Primary Endpoints in Both Phase 3 Clinical Trials in Postpartum Depression," Sage Therapeutics Press Release dated Nov. 9, 2017, 9 pages, ("Thinkstock article").
Aladdin et al., (2008) "Refractory Status Epilepticus During Pregnancy Secondary to Cavernous Angioma," Epilepsia, 49(9):1627-1629.
Allen et al., (2013) "Menstrual Phase, Depressive Symptoms, and Allopregnanolone During Short-Term Smoking Cessation," Experimental and Clinical Psychopharmacology, 21(6):427-433.
Anderson et al., (2014) "Oxidative/Nitrosative Stress and Immunoinflammatory Pathways in Depression: Treatment Implications," Current Pharmaceutical Design, 20(25):4126-4161.
Bancaud et al., (From the Commission on Classification and Terminology of the International League Against Epilepsy) (Aug. 1981) "Proposal for Revised Clinical and Electroencephalographic Classification of Epileptic Seizures," Epilepsia, 22:489-501.
Beckley et al., (2011) "Progesterone receptor antagonist CDB-4124 increases depression-like behavior in mice without affecting locomotor ability," Psychoneuroendocrinology, 36:824-833.
Biagini et al., (2006) "Endogenous neurosteroids modulate epileptogenesis in a model of temporal lobe epilepsy," Experimental Neurology, 201:519-524.
Bleck et al., (2005) "Refractory Status Epileptics", Current Opinion in Critical Care, 11:117-120.
Bobb et al., "Allopregnanolone to Treat Refractory Status Epilepticus," presented at American Clinical Neurophysiology Society (ACNS) Annual Meeting & Courses, The Westin Peachtree Plaza, Atlanta, Georgia, (Feb. 4-9, 2014) Abstract S26.
Broomall et al., (Dec. 2014) "Pediatric Super-Refractory Status Epilipticus Treated with Allopregnanolone," Ann. Neurol, 76:911-915.
Brown et al., (2014) "A Randomized, Double-Blind, Placebo-Controlled Trial of Pregnenolone for Bipolar Depression," Neuropsychopharmacology, 39:2867-2873.

Brunn et al., (2015) "Combined treatment with diazepam and allopregnanolone reverses tetramethylenedisulfotetramine (TETS)-induced calcium dysregulation in cultured neurons and protects TETS-intoxicated mice against lethal seizures," Neuropharmacology, 95:332-342.
Burdock, G.A., (1997) "Encyclopedia of Food Additives and Coloring," Taylor & Francis, 3 Volume Set, p. 2412, 4pp.
Cao et al., (2012) "Tetramethylenedisulfotetramine Alters $Ca^2$ + Dynamics in Cultured Hippocampal Neurons: Mitigation by NMDA Receptor Blockade and $GABA_A$ Receptor-Positive Modulation," Toxicological Sciences, 130(2):362-372.
Chen et al., (1996) "Ibogaine Block of the NMDA Receptor: In Vitro and In Vivo Studies," Neuropharmacology, 35(4):423-431.
Chiasari et al., (2009) "The Influence of Neuroactive Steroid Lipophilicity on GABA Receptor Modulation: Evidence for a Low-Affinity Interaction," Journal of Neurophysiology, 102:1254-1264.
Claassen et al., (2002) "Treatment of Refractory Status Epilepticus with Pentobarbital, Propofol, or Midazolam: A Systematic Review," Epilepsia, 43(2):146-153.
De Crescenzo et al., "Selective serotonin reuptake inhibitors (SSRIs) for post-partum depression (PPD): A systematic review of randomized clinical trials", Journal of Affective Disorders, 152-154 (2014) 39-44.
Deligiannidis et al., (2016) "Peripartum neuroactive steroid and γ-aminobutyric acid profiles in women at-risk for postpartum depression," Psychoneuroendocrinology, Accepted Manuscript, [http://dx.doi.org/10.1016/j.psyneuen.2016.05.010], 33 pages.
Delorenzo et al., (1995) "Epidemiology of Status Epilepticus," Journal of Clinical Neurophysiology, 12(4):316-325.
Deutsch et al., (1996) "Evaluation of In Vivo Interactions in Mice Between Flurazepam and Two Neuroactive Steroids," Pharmacology Biochemistry & Behavior, 55(3):323-326.
Dhir et al., (2012) "Role of neurosteroids in the anticonvulsant activity of midazolam," British Journal of Pharmacology,165(8):2684-2691.
Dhir et al., (2013) "Seizure protection by intrapulmonary delivery of midazolam in mice," Neuropharmacology, 73:425e431.
Dhir et al., (Jan. 2011) "Seizure Protection by Intrapulmonary Delivery of Propofol Hemisuccinate," The Journal of Pharmacology and Experimental Therapeutics, 336(1):215-222.
Finn et al., (1994) "The Estrus Cycle, Sensitivity to Convulsants and the Anticonvulsant Effect of Neuroactive Steroid," The Journal of Pharmacology and Experimental Therapeutics, 271:164-170.
Fitelson et al., "Treatment of postpartum depression: clinical, psychological and pharmacological options", International Journal of Women's Health, 2011, pp. 1-14.
Frank et al., "Neoroprotective effects of allopregnanolone on hippocampal irreversible neurotoxicity in vitro", Prog. Neuro-Psychopharmacol. & Bio. Psychiat. 24:1117-1126, 2000.
Frye et al. (2000) "Infusion of 3α,5α-THP to the pontine reticular formation attenuates PTZ-induced seizures," Brain Research, 881:98-102.
Frye, C.A. (1995) "The neurosteroid 3-α, 5α-THP has antiseizure and possible neuroprotective effects in an animal model of epilepsy," Brain Research, 696:113-120.
Galvin et al., (1987) "Midazolam: an effective intravenous agent for seizure control," Archives of emergency medicine, 4:169-172.
Gasior et al., (1997) "Anticonvulsant and Behavioral Effects of Neuroactive Steroids Alone and in Conjunction with Diazepam," The Journal of Pharmacology and Experimental Therapeutics, The American Society for Pharmacology and Experimental Therapeutics, 282(2):543-553.
Gaynes, B. N. et al., "Perinatal Depression: Prevalence, Screening Accuracy, and Screening Outcomes," Agency for Healthcare Research and Quality (AHRQ) Evidence Report/Technology Assessment No. 119, AHRQ Pub. No. 05-E006-1, Feb. 2005, pp. 1-8.
Gul et al., (2006) "Sterols and the phytosterol content in oilseed rape (*Brassica napus* L.)," Journal of Cell and Molecular Biology, 5:71-79.

(56) References Cited

OTHER PUBLICATIONS

Haas et al., (1992) "Ketamine: A Review of Its Pharmacologic Properties and Use in Ambulatory Anesthesia," Anesthesia, Anesthesia Progress, The American Dental Society of Anesthesiology, 39:61-68.
Hanley et al. (1998) "Use of Midazolam in the treatment of refractory status epilepticus," Clinical Therapeutics, 20(6):1093-1105.
Haut et al., (2002) "Seizure Clustering during Epilepsy Monitoring," Epilepsia, 43(7):711-715.
Haut, (Apr. 2015) "Seizure Clusters: characteristics and treatment," Current Opin. Neurol., 28(2):143-150, [Downloaded on Apr. 7, 2017 from https://www.ncbi.nlm.nih.gov/pubmed/25695133] Abstract only.
Haut, Sheryl R., (2006) "Seizure clustering," Epilepsy & Behavior, 8:50-55.
Hay et al., "Pathways to Violence in the Children of Mothers Who Were Depressed Postpartum", Developmental Psychology, 2003, vol. 39, No. 6, pp. 1083-1094.
He et al., (Jan. 2000) "862.4: Allopregnanolone facilitates spatial learning after traumatic brain injury," Abstracts of the Annual Meeting of the Society for Neuroscience; 30th Annual Meeting of the Society of Neuroscience, Society for Neuroscience, Washington, Dc, Us; New Orleans, LA, USA, 26:2296.
Hellgren et al., (2014) "Low Serum Allopregnanolone Is Associated with Symptoms of Depression in Late Pregnancy," Neuropsychobiology, 69:147-153.
Hincal (2005) "Recent advances in drug delivery using amphiphilic cyclodextrin nanoparticles," European Journal of Pharmaceutical Sciences, 23S1:S3-S4.
Hunter et al., (Mar. 2012) "Status Epilepticus: A Review, With Emphasis on Refractory Cases," Canadian Journal of Neurological Sciences, 39(2):157-169.
Jain et al., (2001) "Hygroscopicity, phase solubility and dissolution of various substituted sulfobutylether β-cyclodextrins (SBE) and danazol-SBE inclusion complexes," International Journal of Pharmaceutics, 212:177-186.
Jones, Ian, "Post-partum depression—a glimpse of light in the darkness?", Published online Jun. 12, 2017 http://dx.doi.org/10.1016/50140-6736(17)31546-5, 2 pages.
Kaminski et al., (2004) "Allopregnanolone Analogs That Positively Modulate $GABA_A$ Receptors Protect against Partial Seizures Induced by 6-Hz Electrical Stimulation in Mice," Epilepsia, 45(7):864-867.
Kanes et al., "Brexanolone (SAGE-547 injection) in post-partum depression: a randomised controlled trial", Lancet, Jul. 29, 2017;390(10093):480-489, and Supplementary Appendix, Published online Jun. 12, 2017, http://dx.doi.org/10.1016/50140-6736(17)31264-3, 20 pages.
Kanes et al., "Open-label, proof-of-concept study of brexanolone in the treatment of severe postpartum depression", Hum Psychopharmacol Clin Exp. 2017;32:e2576. https://doi.org/10.1002/hup.2576, 6 pages; First published Mar. 30, 2017.
Kanto (May/Jun. 1985) Midazolam: The First Water-soluble Benzodiazepine Pharmacology, Pharmacokinetics and Efficacy in Insomnia and Anesthesia, Pharmacotherapy, 5(3):138-155.
Kask et al., (2008) "Allopregnanolone impairs episodic memory in healthy women," Psycopharmacology, vol. 199, pp. 161-168.
Kask et al., (2009) "Allopregnanolone has no effect on startle response and prepulse inhibition of startle response in patients 16 with premenstrual dysphoric disorder or healthy controls," Pharmacology, Biochemistry and Behavior, 92:608-613.
Khanna et al., (2015) "Nanotoxicity: An Interplay of Oxidative Stress, Inflammation and Cell Death," Nanomaterials, 5:1163-1180.
Kim et al., (2011) "Modulation of presynaptic GABAA receptors by endogenous neurosteroids," British Journal of Pharmacology, 164:1698-1710.
Kimmel et al., (2016) "Oxytocin receptor DNA methylation in postpartum depression," Psychoneuroendocrinology, 69:150-160.
Kokate et al. (1994) "Anticonvulsant Activity of Neurosteroids: Correlation with g-Aminobutyric Acid-Evoked Chloride Current Potentiation," The Journal of Pharmacology and Experimental Therapeutics, 270(3):1223-1229.
Kokate et al., (1996) "Neuroactive Steroids Protect Against Pilocarpine- and Kainic Acid-induced Limbic Seizures and Status Epilepticus in Mice," Neuropharmacology, 35(8):1049-1056.
Kokate et al., (1999) "Convulsant actions of the neurosteroid pregnanolone sulfate in mice," Brain Research, 831:119-124.
Kramer, (2012) "Early Ketamine to Treat Refractory Status Epilepticus," Neurocrit. Care, 16:299-305.
Lahiani-Skiba et al., (2005) "Solubility and Dissolution Rate of Progesterone-Cyclodextrin-Polymer Systems," Drug Development and Industrial Pharmacy, 32(9):1043-1058.
Larsen et al., (2005) "Phase Solubility and Structure of the Inclusion Complexes of Prednisolone and 6a-Methyl Prednisolone with Various Cyclodextrins," Journal of Pharmaceutical Sciences, 94(3):507-515.
Leroy et al., (2004) "Pharmacological plasticity of $GABA_A$ receptors at dentate gyrus synapses in a rat model of temporal lobe epilepsy," J. Physol., 557(2):473-487.
Li et al., (Sep. 2010) "Nanoparticle-induced pulmonary toxicity," Experimental Biology and Medicine, 235:1025-1033.
Lonsdale et al., (2007) "The Anticonvulsant effects of allopregnanolone against amygdala-kindled seizures in female rats," Neuroscience Letters, 411:147-151.
Lossin et al., (2012) "Allopregnanolone Treatment in a Rat Pediatric Status Epilepticus Model: Comparison With Diazepam," American Epilepsy Society, (Abst. 3.220) [retrieved on Nov. 29, 2012 from http://www.aesnet.org/go/publications/aes-abstracts/abstract-search/mode/display/st/roga . . . [, 1 page.
Madl et al., (2014) "Nanoparticles, Lung Injury, and the Role of Oxidant Stress," Annu Rev Physiol., 76:447-465.
Maguire et al., (Jul. 31, 2008) "$GABA_AR$ Plasticity during Pregnancy Relevance to Postpartum Depression," Neuron, 59:207-213.
Martini et al., (2000) "Nasal and pulmonary drug delivery systems," Exp. Opin. Ther. Patents, 10(3):315-323.
Masson et al., (2007) "Cyclodextrins and the liquid-liquid phase distribution of progesterone, estrone and prednicarbate," J Ind Phenom Macrocycl Chem, 57:481-487.
Mayer et al., (2002) "Refractory Status Epilepticus Frequency, Risk Factors, and Impact on Outcome," Archives of Neurology, 59:205-210.
Meierkord et al., (2010) "EFNS Guideline on the Management of Status Epilepticus in Adults" European Journal of Neurology, 17:348-355.
Meltzer-Brody et al., "Phase 2 and 3 Studies Evaluating Brexanolone iv, a $GABA_A$ Receptor Positive Allosteric Modulator, in Postpartum Depression", Presented at the 56th Annual Meeting of the American College of Neuropsychopharmacology; Dec. 3, 2017; 14 pages.
Meltzer-Brody et al., "Phase 2 and 3 Studies Evaluating Brexanolone iv, a $GABA_A$ Receptor Positive Allosteric Modulator, in Postpartum Depression", Poster 202B, Presented at the 56th Annual Meeting of the American College of Neuropsychopharmacology; Dec. 3-7, 2017; 1 page.
Melville, "New Drug Shows Rapid, Robust Effect in Postpartum" from https://www.medscape.com/viewarticle/881083, Published Jun. 5, 2017, 2 pages.
Merzlikine et al. (2011) "Development of machine learning models of b-cyclodextrin and sulfobutylether-b-cyclodextrin complexation free energies," International Journal of Pharmaceutics, 418:207-216.
Midazolam Hydrochloride—midazolam hydrochloride injection, solution, EBEWE PARENTA (TM) Pharmaceuticals, Inc., revised 2006, 34pp [Downloaded on Oct. 18, 2017 at file:///C:Users/mhaghighatian/Documents/e-Red%20Folder/13885660New%20folder%2 . . . ].
Miller, "Postpartum Depression", Journal of the American Medical Association (JAMA), Feb. 13, 2002, vol. 287, No. 6, pp. 762-765.
Monagle et al., (2015) "A Phase Ic Trial Comparing the Efficacy and Safety of a New Aqueous Formulation of Alphaxalone with Propofol," Anesthesia & Analgesia, 121(4):914-924.

(56) References Cited

OTHER PUBLICATIONS

Moses Kolko et al., "Antepartum and Postpartum Depression: Healthy Mom, Healthy Baby", Journal of the American Medical Women's Association, 2004; 59: pp. 181-191.
Munari et al., (1979) "The Use of Althesin in Drug-Resistant Status Epilepticus," Epilepsia, 20:475-484.
Murray et al., "Maternal Postnatal Depression and the Development of Depression in Offspring Up to 16 Years of Age", Journal of the American Academy of Child & Adolescent Psychiatry, 2011; 50 (5), pp. 460-470.
Murray et al., "Prediction, detection, and treatment of post natal depression", Archives of Disease in Childhood, The Journal of the Royal College of Paediatrics and Child Health, 1997, 77: 97-101.
Nanjwade et al., (Sep.-Oct. 2011) "Pulmonary Drug Delivery: Novel Pharmaceutical Technologies Breathe New Life into the Lungs," PDA J Pharm Sci and Tech, [Downloaded from journal. pda.org on Oct. 8, 2015] 65:513-534.
Nin et al., (2012) "The effect of intra-nucleus accumbens administration of allopregnanolone on δ and γ2 $GABA_A$ receptor subunit mRNA expression in the hippocampus and on depressive-like and grooming behaviors in rats," Pharmacology, Biochemistry and Behavior, 103:359-366.
Northdurfter et al., "Recent Developments in Potential Anxiolytic Agents Targeting $GABA_A$/BzR Complex or the Translocator Protein (18kDa) (TSPO)", Current Topics in Medicinal Chemistry, 2012, 12; pp. 360-370.
Novy et al., (2010) "Refractory Status Epilepticus: A Prospective Observational Study," Epilepsia, 51(2):251-256.
Oka et al. (2006) "A Reliable Method for Intratracheal Instillation of Materials to the Entire Lung in Rats," J Toxicol Pathol, 19:107-109.
Osborne et al., (2015) "Replication of Epigenetic Postpartum Depression Biomarkers and Variation with Hormone Levels," Neuropsychopharmacology, accepted article preview Oct. 27, 2015; Accepted Manuscript, [doi: 10.1038/npp.2015.333], 32pp.
Park et al., (2011) "Multiple effects of allopregnanolone on GABAergic responses in single hippocampal CA3 pyramidal neurons," European Journal of Pharmacology, 652:46-54.
Pieribone et al., (2007) "Clinical Evaluation of Ganaxolone in Pediatric and Adolescent Patients with Refractory Epilepsy", Epilepsia, 48(10):1870-1874.
Pires et al. (2009) "Intranasal Drug Delivery: How, Why and What for?" J Pharm Pharmaceut Sci, 12(3):288-311.
PubChem CID 92786, AllopregnanoloneIC2iH34O2, [Retrieved online on Dec. 7, 2015 at <URL:https://pubchem.ncbi.nlm.nih.gov/compound/92786#section= Top>], 20 pages.
Ramsay, Eugene R., (1993) "Treatment of Status Epilepticus," Epilepsia, 34(Suppl. 1):571-581.
Reddy (Oct. 2011), "Role of anticonvulsant and antiepileptogenic neurosteroids in the pathophysiology and treatment of epilepsy," Frontiers in Endocrinology, 2:38, llpp [Published online Oct. 5, 2011, doi: 10.3389/fendo.2011.00038; Pre-published online Aug. 9, 2011].
Reddy (Sep. 2013), "SGE-102: a novel therapy for refractory status epilepticus," Epilepsia, Abstract, 54 Suppl 6:81-83, 2 pages [retrieved on Sep. 7, 2015 at http://www.ncbi.nlm.nih.gov/pubmed/24001082].
Reddy et al. (2012) "Neurosteroids—Endogenous Regulators of Seizure Susceptibility and Role in Treatment of Epilepsy,", Jasper's Basic Mechanisms of the Epilepsies Fourth Edition, pp. 1-23.
Rogawski et al., (Sep. 2013) "Neuroactive Steroids for the Treatment of Status Epilepticus," Epilepsia, Author manuscript; available in PMC Sep. 1, 2014, 54(0 6): 93-98, doi:10.1111/epi.12289.
Rosenthal et al. (2017) "Brexanolone as Adjunctive Therapy in Super-Refractory Status Epilepticus," Annals of Neurology, John Wiley & Sons, [Accepted Article, doi: 10. 1002/ana.25008] 32pp.
Rosseti et al. (2011) "A Randomized Trial for the Treatment of Refractory Status Epilepticus," Neurocritical Care Society, 14(1):4-10.
Saddy et al., (1979) "Case Report: Althesin in Status Epilepticus," Aneasth. Intens. Care, 7(3):267-270.
Sahin et al., (2001) "Outcome of Severe Refractory Status Epilepticus in Children," Epilepsia, 41(11):1461-1467.
Sanborn et al. (May 28, 2002) "Identifying and managing adverse environmental health effects: 4. Pesticides," CMAJ, 166(11):1431-1436.
Santoru et al., (2014) "Decreased allopregnanolone induced by hormonal contraceptives is associated with a reduction in social behavior and sexual motivation in female rats," Psychopharmacology, 14 pages.
Schiller et al. (2014) "Allopregnanolone as a mediator of affective switching in reproductive mood disorders," Psychopharmacology, 11 pages.
Schiller et al., (2015) "The role of reproductive hormones in postpartum depression," CNS Spectrums, 20(1):48-59.
Schule et al. (2014) "The role of allopregnanolone in depression and anxiety," Progress in Neurobiology, 113:79-87.
Shah et al., (2001) "Peripheral WBC Count and Serum Prolactin Level in Various Seizure Types and Nonepileptic Events," Epilepsia, 42(11):1472-1475.
Shimizu et al., (2015) "Allopregnanolone Increases Mature Excitatory Synapses Along Dendrites Via Protein Kinase A Signaling," Neuroscience, 305:139-145.
Shorvon et al. (2012) "The Outcome of Therapies in Refractory and Super-Refractory Convulsive Status Epilepticus and Recommendations for Therapy," Brain, 135(8):2134-2328.
Shorvon et al., (2007) "The Proceedings of the First London Colloquium on Status Epilepticus- University College London, Apr. 12-15, 2007," Epilepsia, 48(8):1-3.
Shorvon et al., (Oct. 2011) "The treatment of super-refractory status epilepticus: a critical review of available therapies and a clinical treatment protocol," Brain, A Journal of Neurology, 134, No. 10, pp. 2802-2818.
Smith et al., (2013) "The Influence of Stress At Puberty on Mood and Learning: Role of the α4βδ GABAA Receptor," Neuroscience, 249:192-213.
Timby et al., (2006) "Pharmacokinetic and behavioral effects of allopregnanolone in healthy women," Psycopharmacology, 186(3):414-424.
Timby et al., (2016) "Women with premenstrual dysphoric disorder have altered sensitivity to allopregnanolone over the menstrual cycle compared to controls—a pilot study," Psychopharmacology, 233:2109-2117.
Tolmacheva et al., (2007) "The role of ovarian steroid hormones in the regulation of basal and stress induced absence seizures," Journal of Steroid Biochemistry & Molecular Biology, 104:281-288.
Tongiani et al., (2009) "Sulfobutyl Ether-Alkyl Ether Mixed Cyclodextrin Derivatives With Enhanced Inclusion Ability", Journal of Pharmaceutical Sciences, 98(12):4769-4780.
Turkmen et al., (2011) "Tolerance to Allopregnanolone with Focus on the GABA-A Receptor," British Journal of Pharmacology, 162:311-327.
Ueda et al. (2008) "Evaluation of a Sulfobutyl Ether β-Cyclodextrin as a Aolubilizing/Stabilizing Agent for Several Drugs," Drug Development and Industrial Pharmacy, 24(9):863-867.
Vaitkevicius et al., (2013) "Successful Allopregnanolone Treatment of New Onset Refractory Status Epilepticus (Norse) Syndrome: First in Man Experience," Epilepsia, Abstract, P29, p. 114.
Vaitkevicius et al., (2017) "First-in-man allopregnanolone use in super-refractory status epilepticus," Annals of Clinical and Translational Neurology, 4(6):411-414 [doi: 10.1002/acn3.408].
Vanlandingham et al., (2008) "Progesterone and its metabolite allopregnanolone differentially regulate hemostatic proteins after traumatic brain injury," Journal of Cerebral Blood Flow & Metabolism, 28:1786-1794.
Weisberg et al., (1983) "Seizure Disorders," Essentials of Clinical Neurology, Chapter 11, pp. 167-175.
Wolkowitz et al., "Of sound mind and body: depression, disease, and accelerated aging", Dialogues Clin Neurosci. 13(1):25-39, 2011.

(56) References Cited

OTHER PUBLICATIONS

Zhu et al., (2001) "Evaluation and comparison of the pharmacokinetic and pharmacodynamic properties of allopregnanolone and pregnanolone at induction of anaesthesia in the male rat," British Journal of Anaesthesia, 86(3):403-412.

Zia et al., (1996) "Effect of Alkyl Chain and Degree of Substitution on the Complexation of Sulfoalkyl Ether β-Cyclodextrins with Steroids," Journal of Pharmaceutical Sciences, 86(2):220-224.

Zia et al., (2000) "Thermodynamics of Binding of Neutral Molecules to Sulfobutyl Ether β-Cyclodextrins (SBE-β-CDs): The Effect of Total Degree of Substitution," Pharmaceutical Research, 17(8):936-941.

Zia et al., (2001) "Effect of Cyclodextrin Charge on Complexation of Neutral and Charged Substrates: Comparison of (SBE) 7M-β-CD to HP-β-CD," Pharmaceutical Research, 18(5):667-673.

Zolkowska et al., "Anticonvulsant Activity of Intravenous and Intramuscular Allopregnenalone," *American Epilepsy Society*, (Abst. 1.023), 2012, Published to Web: Sep. 6, 2012, Source: www.aesnet.org, Annual Meeting Abstracts: View, 2 pages.

Zolkowska et al., (2012) "Anticonvulsant Activity of Intravenous and Intramuscular Allopregnenalone," American Epilepsy Society, (Poster), UC Davis, University of California, 1 page.

Zolkowska et al., (2012) "Anticonvulsant Activity of Intravenous and Intramuscular Allopregnenalone," American Epilepsy Society, (Abst. 1.023) [retrieved on Nov. 29, 2012 from http://www.aesnet.org/go/publications/aes-abstracts/abstract-search/mode/display/st/roga . . . ], 1 page.

Zonana et al., "The Neurobiology of Postpartum Depression", CNS Spectrums, Oct. 2005, vol. 10, No. 10, pp. 792-799, 805.

Zsuzsa Aszalos, "Neurological and psychiatric aspects of some endocrine diseases. The role of neurosteroids and neuroactive steroids," Ory Hetil, Oct. 14, 2007, 148(41):1929-1937, with machine translation into English.

"Allopregnanolone for the Treatment of Traumatic Brain Injury", ClinicalTrials.gov Identifier: NCT01673828; First Posted: Aug. 28, 2012; retrieved on Jan. 10, 2019; 7 pages.

* cited by examiner

ANTICONVULSANT ACTIVITY OF STEROIDS

CROSS-REFERENCE TO RELATED APPLICATIONS

This application is a continuation of U.S. application Ser. No. 15/632,360, filed on Jun. 25, 2017, which is a continuation of U.S. application Ser. No. 14/646,886, filed on May 22, 2015, which is a U.S. national phase application under 35 U.S.C. § 371 of International Appl. No. PCT/US2013/072351, filed on Nov. 27, 2013, which claims the benefit under 35 U.S.C. § 119(e) of U.S. Provisional Application No. 61/732,252, filed on Nov. 30, 2012, all of which are hereby incorporated herein by reference in their entireties for all purposes.

FIELD

The present invention relates to methods of preventing, inhibiting, delaying, and/or mitigating seizures by administration of a steroid, e.g., a neurosteroid, e.g., allopregnanolone.

BACKGROUND

Steroids, including neurosteroids (e.g., allopregnanolone) are highly insoluble in aqueous solution. Various approaches are used to enhance aqueous dissolution, including the use of cyclodextrin solutions. However, even with cyclodextrin as a solvation aid, solubility is not sufficient to permit systemic delivery for the treatment of medical conditions.

SUMMARY

In one aspect, methods of preventing, treating, reducing, and/or mitigating one or more symptoms associated with and/or caused by traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, and smoking cessation in a subject in need thereof are provided. In some embodiments, the methods comprise administering to the subject a steroid.

In another aspect, methods of preventing, treating, reducing, and/or mitigating symptoms associated with and/or caused by epilepsy, in a subject in need thereof are provided. In some embodiments, the methods comprise administering to the subject a steroid.

In a further aspect, methods of accelerating the termination or abortion of an impending seizure in a subject in need thereof are provided. In some embodiments, the methods comprise administering to the subject a steroid.

With respect to embodiments of the methods, in some embodiments, the steroid is a neurosteroid. In some embodiments, the neurosteroid is selected from the group consisting of allopregnanolone, allotetrahydrodeoxycorticosterone, ganaxolone, alphaxolone, alphadolone, hydroxydione, minaxolone, and Althesin. In some embodiments, the neurosteroid is allopregnanolone. In some embodiments, the steroid is formulated in a cyclodextrin. In various embodiments, the steroid is formulated in hydroxypropyl-beta-cyclodextrin or sulfobutylether-beta-cyclodextrin sodium salt. In some embodiments, the subject is experiencing aura. In some embodiments, the subject has been warned of an impending seizure. In some embodiments, the subject is experiencing a seizure. In some embodiments, the subject has status epilepticus. In some embodiments, the subject has myoclonic epilepsy. In some embodiments, the subject suffers from seizure clusters. In some embodiments, the seizure is a tonic seizure. In some embodiments, the seizure is a clonic seizure. In some embodiments, the subject is a human. In some embodiments, the steroid is administered intramuscularly, intravenously or subcutaneously. In some embodiments, the methods entail treating, reducing, and/or mitigating symptoms associated with and/or caused by epilepsy by intramuscularly (i.m.), subcutaneously (s.c.) or intravenously (i.v.) administering allopregnanolone formulated in a sulfobutylether-beta-cyclodextrin sodium salt. In some embodiments, the epilepsy is status epilepticus. In some embodiments, the steroid or neurosteroid (e.g., allopregnanolone) is administered at a dose in the range of about 0.25 mg/kg to about 15 mg/kg, e.g., about 0.25, 0.5, 1, 2, 3, 4, 5, 6, 7, 8, 9, 10, 11, 12, 13, 14, 15 mg/kg. In some embodiments, the steroid or neurosteroid (e.g., allopregnanolone) is self-administered by the subject. In some embodiments, the steroid or neurosteroid (e.g., allopregnanolone) is administered by a caregiver who is not the subject.

In a further aspect, compositions comprising or consisting essentially of a steroid and a cyclodextrin are provided. In some embodiments, the steroid is a neurosteroid. In some embodiments, the neurosteroid is selected from the group consisting of allopregnanolone, allotetrahydrodeoxycorticosterone, ganaxolone, alphaxolone, alphadolone, hydroxydione, minaxolone, and Althesin. In some embodiments, the steroid is allopregnanolone. In some embodiments, the cyclodextrin is hydroxypropyl-beta-cyclodextrin, sulfobutylether-beta-cyclodextrin sodium salt, or mixture thereof. In some embodiments, the composition comprises allopregnanolone and sulfobutylether-beta-cyclodextrin sodium salt.

In some embodiments, the steroid or neurosteroid (e.g., allopregnanolone) is administered or formulated for administration via an inhaler. In some embodiments, the steroid or neurosteroid (e.g., allopregnanolone) is nebulized or aerosolized. In some embodiments, the steroid or neurosteroid (e.g., allopregnanolone) is nebulized or aerosolized without heating. In some embodiments, the nebulized or aerosolized steroid or neurosteroid (e.g., allopregnanolone) particles have a mass median aerodynamic diameter ("MMAD") of about 5 μm or smaller. In some embodiments, the nebulized or aerosolized steroid or neurosteroid (e.g., allopregnanolone) particles have a mass median aerodynamic diameter ("MMAD") of about 2-3 μm. In some embodiments, the steroid or neurosteroid (e.g., allopregnanolone) is delivered to the distal alveoli.

Definitions

As used herein, "administering" refers to local and systemic administration, e.g., including enteral, parenteral, pulmonary, and topical/transdermal administration. Routes of administration for steroid or neurosteroids (e.g., allopregnanolone) that find use in the methods described herein include, e.g., oral (per os (P.O.)) administration, nasal, inhalation or intrapulmonary administration, administration as a suppository, topical contact, transdermal delivery (e.g., via a transdermal patch), intrathecal (IT) administration, intravenous ("iv") administration, intraperitoneal ("ip") administration, intramuscular ("im") administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The term "co-administration" refers to the presence of both active agents in the blood at the same time. Active agents that are co-administered can be delivered concurrently (i.e., at the same time) or sequentially.

The phrase "cause to be administered" refers to the actions taken by a medical professional (e.g., a physician), or a person controlling medical care of a subject, that control and/or permit the administration of the steroid or neurosteroid (e.g., allopregnanolone) to the subject. Causing to be administered can involve diagnosis and/or determination of an appropriate therapeutic or prophylactic regimen, and/or prescribing particular steroid or neurosteroid (e.g., allopregnanolone) for a subject. Such prescribing can include, for example, drafting a prescription form, annotating a medical record, and the like.

The term "effective amount" or "pharmaceutically effective amount" refer to the amount and/or dosage, and/or dosage regime of one or more steroid or neurosteroid (e.g., allopregnanolone) necessary to bring about the desired result e.g., an amount sufficient prevent, abort or terminate a seizure.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The terms "reduce," "inhibit," "relieve," "alleviate" refer to the detectable decrease in the frequency, severity and/or duration of seizures. A reduction in the frequency, severity and/or duration of seizures can be measured by self-assessment (e.g., by reporting of the patient) or by a trained clinical observer. Determination of a reduction of the frequency, severity and/or duration of seizures can be made by comparing patient status before and after treatment.

The term "mitigating" refers to reduction or elimination of one or more symptoms of that pathology or disease, and/or a reduction in the rate or delay of onset or severity of one or more symptoms of that pathology or disease (e.g., seizures), and/or the prevention of that pathology or disease.

As used herein, the phrase "consisting essentially of" refers to the genera or species of active pharmaceutical agents (e.g., neurosteroid, e.g., allopregnanolone) and excipient (e.g., hydroxypropyl-beta-cyclodextrin or Captisol (sulfobutylether-beta-cyclodextrin sodium salt)) included in a method or composition. In various embodiments, other unmentioned or unrecited active ingredients and inactive are expressly excluded. In various embodiments, additives (e.g., surfactants, acids (organic or fatty), alcohols, esters, co-solvents, solubilizers, lipids, polymers, glycols) are expressly excluded.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other healthworker in a hospital, psychiatric care facility, as an outpatient, or other clinical context. In certain embodiments the subject may not be under the care or prescription of a physician or other healthworker.

The term "neuroactive steroid" or "neurosteroid" refers to steroid compounds that rapidly alter neuronal excitability through interaction with neurotransmitter-gated ion channels. Neurosteroids act as allosteric modulators of neurotransmitter receptors, such as $GABA_A$, NMDA, and sigma receptors. Neurosteroids find use as sedatives for the purpose of general anaesthesia for carrying out surgical procedures, and in the treatment of epilepsy and traumatic brain injury. Illustrative neurosteroids include, e.g., allopregnanolone, Ganaxolone, alphaxolone, alphadolone, hydroxydione, minaxolone, and Althesin (a mixture of alphaxolone and alphadolone).

DETAILED DESCRIPTION

1. Introduction

Figure 1:
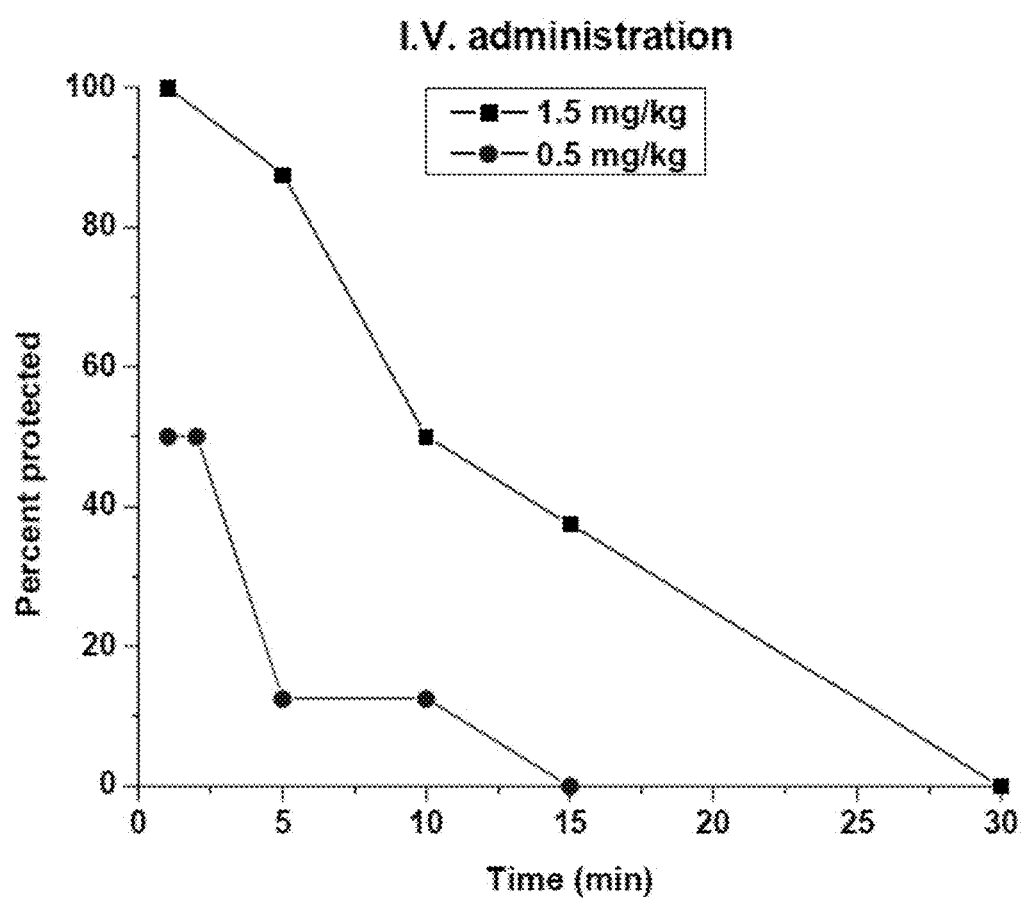
FIG. 1 illustrates a time course for protection by allopregnanolone (5α,3α-P) administered i.v. at a doses of 1.5 and 0.5 mg/kg respectively in the 6-Hz electrical-stimulation (32 mA, 3 s) model. The interval between the steroid injection and the electrical stimulus is plotted on the abscissa and the percentage of animals protected against seizures is plotted on the ordinate. Each point represents eight mice.

Treatment of status epilepicus requires rapid administration of anti-seizure agents, which are typically delivered either by the intravenous (IV) or intramuscular (IM) routes. Allopregnanolone (3α-hydroxy-5α-pregnan-20-one; 5α,3α-P), an endogenous progesterone-derived steroid that is a positive allosteric modulator of $GABA_A$ receptors, is a powerful anti-seizure agent with potential in the treatment of status epilepticus. The present study determines and demonstrates the dosing of allopregnanolone to protect against seizures when delivered intravenously (i.v.), intramuscularly (i.m.), subcutaneously (s.c.) or orally (p.o.).

2. Subjects Who can Benefit

In various embodiments, the subject has a condition that can be treated or mitigated by administration of a neurosteroid, e.g., allopregnanolone. Allopregnanolone has many medical uses, including the treatment, reduction, and/or mitigation of symptoms associated with and/or caused by traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, and smoking cessation. The subject may or may not be exhibiting symptoms.

Accordingly, the invention also contemplates methods of treating, reducing, and/or mitigating symptoms associated with and/or caused by traumatic brain injury, Alzheimer's disease, epilepsy, anxiety, fragile X syndrome, post-traumatic stress disorder, lysosomal storage disorders (Niemann-Pick type C disease), depression (including post-partum depression), premenstrual dysphoric disorder, alcohol craving, and smoking cessation by administration of a steroid or neurosteroid (e.g., allopregnanolone) dissolved or suspended in a vehicle suitable for systemic administration (e.g., intramuscular, intravenous, subcutaneous), as described herein.

In some embodiments, the subject has epilepsy, has a history of suffering from epileptic seizures or is suffering from epileptic seizures. In various embodiments, the patient may be experiencing an electrographic or behavioral seizure or may be experiencing a seizure aura, which itself is a localized seizure that may spread and become a full blown behavioral seizure. For example, the subject may be experiencing aura that alerts of the impending onset of a seizure or seizure cluster.

Alternatively, the subject may be using a seizure prediction device that alerts of the impending onset of a seizure or seizure cluster. Implantable seizure prediction devices are known in the art and described, e.g., in D'Alessandro, et al., IEEE TRANSACTIONS ON BIOMEDICAL ENGINEERING, VOL. 50, NO. 5, MAY 2003, and U.S. Patent Publication Nos. 2010/0198098, 2010/0168603, 2009/0062682, and 2008/0243022.

The subject may have a personal or familial history of any of the epileptic conditions described herein. The subject may have been diagnosed as having any of the epileptic conditions described herein. In some embodiments, the subject has or is at risk of suffering a myoclonic seizure or myoclonic epilepsy, e.g., juvenile myoclonic epilepsy. The PTZ seizure model demonstrated herein is predictive of utility and/or activity in counteracting myoclonic seizures or myoclonic epilepsy in humans.

In various embodiments, the subject may be at risk of exposure to or may have been exposed to a nerve agent or a pesticide that can cause seizures. Illustrative nerve agents that can cause seizures include, e.g., organophosphorus nerve agents, e.g., tabun, sarin, soman, GF, VR and/or VX. Illustrative pesticides that can cause seizures include, e.g., organophosphate pesticides (e.g., Acephate (Orthene), Azinphos-methyl (Gusathion, Guthion), Bensulide (Betasan, Lescosan), Bomyl (Swat), Bromophos (Nexion), Bromophos-ethyl (Nexagan), Cadusafos (Apache, Ebufos, Rugby), Carbophenothion (Trithion), Chlorethoxyfos (Fortress), Chlorfenvinphos (Apachlor, Birlane), Chlormephos (Dotan), Chlorphoxim (Baythion-C), Chlorpyrifos (Brodan, Dursban, Lorsban), Chlorthiophos (Celathion), Coumaphos (Asuntol, Co-Ral), Crotoxyphos (Ciodrin, Cypona), Crufomate (Ruelene), Cyanofenphos (Surecide), Cyanophos (Cyanox), Cythioate (Cyflee, Proban), DEF (De-Green), E-Z-Off D), Demeton (Systox), Demeton-S-methyl (Duratox, Metasystoxl), Dialifor (Torak), Diazinon, Dichlorofenthion, (VC-13 Nemacide), Dichlorvos (DDVP, Vapona), Dicrotophos (Bidrin), Dimefos (Hanane, Pestox XIV), Dimethoate (Cygon, DeFend), Dioxathion (Delnav), Disulfoton (Disyston), Ditalimfos, Edifenphos, Endothion, EPBP (S-seven), EPN, Ethion (Ethanox), Ethoprop (Mocap), Ethyl parathion (E605, Parathion, thiophos), Etrimfos (Ekamet), Famphur (Bash, Bo-Ana, Famfos), Fenamiphos (Nemacur), Fenitrothion (Accothion, Agrothion, Sumithion), Fenophosphon (Agritox, trichloronate), Fensulfothion (Dasanit), Fenthion (Baytex, Entex, Tiguvon), Fonofos (Dyfonate, N-2790), Formothion (Anthio), Fosthietan (Nem-A-Tak), Heptenophos (Hostaquick), Hiometon (Ekatin), Hosalone (Zolone), IBP (Kitazin), Iodofenphos (Nuvanol-N), Isazofos (Brace, Miral, Triumph), Isofenphos (Amaze, Oftanol), Isoxathion (E-48, Karphos), Leptophos (Phosvel), Malathion (Cython), Mephosfolan (Cytrolane), Merphos (Easy Off-D, Folex), Methamidophos (Monitor), Methidathion (Supracide, Ultracide), Methyl parathion (E601, Penncap-M), Methyl trithion, Mevinphos (Duraphos, Phosdrin), Mipafox (Isopestox, Pestox XV), Monocrotophos (Azodrin), Naled (Dibrome), Oxydemeton-methyl (Metasystox-R), Oxydeprofos (Metasystox-S), Phencapton (G 28029), Phenthoate (Dimephenthoate, Phenthoate), Phorate (Rampart, Thimet), Phosalone (Azofene, Zolone), Phosfolan (Cylan, Cyolane), Phosmet (Imidan, Prolate), Phosphamidon (Dimecron), Phostebupirim (Aztec), Phoxim (Baythion), Pirimiphos-ethyl (Primicid), Pirimiphos-methyl (Actellic), Profenofos (Curacron), Propetamphos (Safrotin), Propyl thiopyrophosphate (Aspon), Prothoate (Fac), Pyrazophos (Afugan, Curamil), Pyridaphenthion (Ofunack), Quinalphos (Bayrusil), Ronnel (Fenchlorphos, Korlan), Schradan (OMPA), Sulfotep (Bladafum, Dithione, Thiotepp), Sulprofos (Bolstar, Helothion), Temephos (Abate, Abathion), Terbufos (Contraven, Counter), Tetrachlorvinphos (Gardona, Rabon), Tetraethyl pyrophosphate (TEPP), Triazophos (Hostathion), and Trichlorfon (Dipterex, Dylox, Neguvon, Proxol).

3. Steroids

The compositions generally comprise or consist essentially of a steroid, e.g., a neurosteroid, suspended or dissolved in vehicle appropriate for systemic administration, e.g., a cyclodextin, e.g., hydroxypropyl-beta-cyclodextrin or sulfobutylether-beta-cyclodextrin sodium salt, or mixtures thereof.

In various embodiments the neurosteroid is allopregnanolone (ALP). Allopregnanolone, also known as 3α-hydroxy-5α-pregnan-20-one or 3α,5α-tetrahydroprogesterone, IUPAC name 1-(3-Hydroxy-10,13-dimethyl-2,3,4,5,6,7,8,9,11,12,14,15,16,17-tetradecahydro-1H-cyclopenta[a]phenanthren-17-yl)ethanone, and referenced as CAS number 516-54-1, is a prototypic neurosteroid present in the blood and also the brain. It is a metabolite of progesterone and modulator of $GABA_A$ receptors. While allopregnanolone, like other $GABA_A$ receptor active neurosteroids such as allotetrahydrodeoxycorticosterone (3α,21-dihydroxy-5α-pregnan-20-one; THDOC), positively modulates all $GABA_A$ receptor isoforms, those isoforms containing δ-subunits exhibit greater magnitude potentiation. Allopregnanolone has pharmacological properties similar to other positive modulators of $GABA_A$ receptors, including anxiolytic and anticonvulsant activity. Allopregnanolone is neuroprotective in many animal models of neurodegenerative conditions, including, e.g., Alzheimer's disease (Wang et al., Proc Natl Acad Sci USA. 2010 Apr. 6; 107(14):6498-503), cerebral edema (Limmroth et al., Br J Pharmacol. 1996 January; 117(1):99-104) and traumatic brain injury (He et al., Restor Neurol Neurosci. 2004; 22(1):19-31; and He, et al., Exp Neurol. 2004 October; 189(2):404-12), Mood disorders (Robichaud and Debonnel, Int J Neuropsychopharmacol. 2006 April; 9(2):191-200), Niemann-Pick type C disease (Griffin et al., Nat Med. 2004 July; 10(7):704-11) and acts as an anticonvulsant against chemically induced seizures, including the pentylenetetrazol (PTZ) model (Kokate et al., J Pharmacol Exp Ther. 1994 September; 270(3):1223-9). The chemical structure of allopregnanolone is depicted below in Formula I:

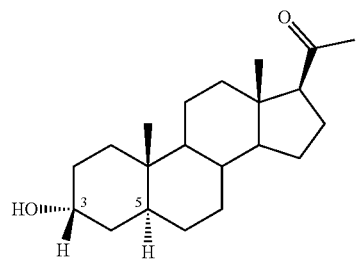

In various embodiments, the compositions comprise a sulfate, salt, hemisuccinate, nitrosylated, derivative or congener of allopregnanolone.

Other neurosteroids that can be formulated in vehicle suitable for systemic administration, include without limitation allotetrahydrodeoxycorticosterone (3α,21-dihydroxy-5α-pregnan-20-one; THDOC), 3 α,21-dihydroxy-5b-pregnan-20-one, pregnanolone (3α-hydroxy-5β-pregnan-20-one), Ganaxolone (INN, also known as CCD-1042; IUPAC name (3α,5α)-3-hydroxy-5-methylpregnan-20-one; 1-[(3R,5S,8R,9S,10S,13S,14S,17S)-3-hydroxy-3,10,13-trimethyl-1,2,4,5,6,7,8,9,11,12,14,15,16,17-tetradecahydrocyclopenta[a]phenanthren-17-yl]ethanone), alphaxolone, alphadolone, hydroxydione, minaxolone, and Althesin (a mixture of alphaxolone, alphadolone, tetrahydrodeoxycorticosterone, pregnenolone, dehydroepiandrosterone (DHEA), 7-substituted benz[e]indene-3-carbonitriles (see, e.g., Hu, et al., J Med Chem. (1993) 36(24):3956-67); 7-(2-hydroxyethyl)benz[e]indene analogues (see, e.g., Han, et al., J Med Chem. (1995) 38(22):4548-56); 3 alpha-hydroxy-5 alpha-pregnan-20-one and 3 alpha-hydroxy-5 beta-pregnan-20-one analogues (see, e.g., Han, et al., J Med Chem. (1996) 39(21):4218-32); enantiomers of dehydroepiandrosterone sulfate, pregnenolone sulfate, and (3alpha,5beta)-3-hydroxypregnan-20-one sulfate (see, e.g., Nilsson, et al., J Med Chem. (1998) 41(14):2604-13); 13,24-cyclo-18,21-dinorcholane analogues (see, e.g., Jiang, et al., J Med Chem. (2003) 46(25):5334-48); N-acylated 17a-aza-D-homosteroid analogues (see, e.g., Covey, et al., J Med Chem. (2000) 43(17):3201-4); 5 beta-methyl-3-ketosteroid analogues (see, e.g., Zeng, et al., J Org Chem. (2000) 65(7):2264-6); 18-norandrostan-17-one analogues (see, e.g., Jiang, et al., J Org Chem. (2000) 65(11):3555-7); (3alpha,5alpha)- and (3alpha,5beta)-3-hydroxypregnan-20-one analogs (see, e.g., Zeng, et al., J Med Chem. (2005) 48(8):3051-9); benz[f]indenes (see, e.g., Scaglione, et al., J Med Chem. (2006) 49(15):4595-605); enantiomers of androgens (see, e.g., Katona, et al., Eur J Med Chem. (2008) 43(1):107-13); cyclopenta[b]phenanthrenes and cyclopenta[b]anthracenes (see, e.g., Scaglione, et al., J Med Chem. (2008) 51(5):1309-18); 2beta-hydroxygonane derivatives (see, e.g., Wang, et al., Tetrahedron (2007) 63(33):7977-7984); Δ16-alphaxalone and corresponding 17-carbonitrile analogues (see, e.g., Bandyopadhyaya, et al., Bioorg Med Chem Lett. (2010) 20(22):6680-4); Δ(16) and Δ(17(20)) analogues of Δ(16)-alphaxalone (see, e.g., Stastna, et al., J Med Chem. (2011) 54(11):3926-34); neurosteroid analogs developed by CoCensys (now Purdue Neuroscience) (e.g., CCD-3693, Co2-6749 (a.k.a., GMA-839 and WAY-141839); neurosteroid analogs described in U.S. Pat. No. 7,781,421 and in PCT Patent Publications WO 2008/157460; WO 1993/003732; WO 1993/018053; WO 1994/027608; WO 1995/021617; WO 1996/016076; WO 1996/040043, as well as salts, hemisuccinates, nitrosylated, sulfates and derivatives thereof.

In various embodiments, the steroid or neurosteroid is not a sex hormone. In various embodiments, the steroid or neurosteroid is not progesterone.

As appropriate, the steroid or neurosteroid (e.g., allopregnanolone) may or may not be micronized. As appropriate, the steroid or neurosteroid (e.g., allopregnanolone) may or may not be enclosed in microspheres in suspension in the oil.

4. Formulation and Administration

In varying embodiments, the steroid and/or an analog thereof can be administered systemically, e.g., intramuscularly (IM), or depo-IM, subcutaneously (SQ), and depo-SQ), as appropriate or desired. In varying embodiments, the dosage form is selected to facilitate delivery to the brain (e.g., passage through the blood brain barrier). In this context it is noted that the steroids or neurosteroids (e.g., allopregnanolone) described herein can be readily delivered to the brain. Dosage forms known to those of skill in the art are suitable for delivery of the steroid.

Compositions are provided that contain therapeutically effective amounts of the steroid or neurosteroid (e.g., allopregnanolone). The steroids or neurosteroids (e.g., allopregnanolone) are preferably formulated into suitable pharmaceutical preparations such as tablets, capsules, or elixirs for oral administration or in sterile solutions or suspensions for parenteral administration. Typically the steroids or neurosteroids (e.g., allopregnanolone) described above are formulated into pharmaceutical compositions using techniques and procedures well known in the art.

These steroids or neurosteroids (e.g., allopregnanolone) or analogs thereof can be administered in the "native" form or, if desired, in the form of salts, esters, amides, prodrugs, derivatives, and the like, provided the salt, ester, amide, prodrug or derivative is suitable pharmacologically effective, e.g., effective in the present method(s). Salts, esters, amides, prodrugs and other derivatives of the active agents can be prepared using standard procedures known to those skilled in the art of synthetic organic chemistry and described, for example, by March (1992) Advanced Organic Chemistry; *Reactions, Mechanisms and Structure,* 4th Ed. N.Y. Wiley-Interscience.

Methods of formulating such derivatives are known to those of skill in the art. For example, the disulfide salts of a number of delivery agents are described in PCT Publication WO 2000/059863 which is incorporated herein by reference. Similarly, acid salts of therapeutic peptides, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, orotic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the pHmax to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments preparation of esters typically involves functionalization of hydroxyl and/or carboxyl groups that are present within the molecular structure of the active agent. In certain embodiments, the esters are typically acyl-substituted derivatives of free alcohol groups, e.g., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

Determination of an effective amount for administration in a single dosage is well within the capability of those skilled in the art, especially in light of the detailed disclosure provided herein. Generally, an efficacious or effective amount of the steroid or neurosteroid (e.g., allopregnanolone) is determined by first administering a low dose or small amount of the agent and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in Brunton, et al., *Goodman and Gilman's The Pharmacological Basis of Therapeutics,* 12th Edition, 2010, McGraw-Hill Professional; in a *Physicians' Desk Reference* (PDR), 66th Edition, 2012; in Loyd, et al., *Remington: The Science and Practice of Pharmacy*, 22st Ed., 2012, Pharmaceutical Press; in *Martindale: The Complete Drug Reference*, Sweetman, 2005, London: Pharmaceutical Press., and in Martindale, *Martindale: The Extra Pharmacopoeia*, 31st Edition., 1996, Amer Pharmaceutical Assn, each of which are hereby incorporated herein by reference. In various embodiments, the compositions are formulated, e.g., for oral administration, at a dose in the range of about 5 mg/kg to about 250 mg/kg of the steroid or neurosteroid (e.g., allopregnanolone), e.g., about 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 75 mg/kg, 100 mg/kg, 125 mg/kg, 150 mg/kg, 200 mg/kg, or 250 mg/kg.

About 1 to 1000 mg of a steroid or neurosteroid (e.g., allopregnanolone), or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 1-1000 mg, 2-800 mg, 5-500 mg, 10-400 mg, 50-200 mg, e.g., about 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 200 mg, 300 mg, 400 mg, 500 mg, 600 mg, 700 mg, 800 mg, 900 mg or 1000 mg of the active ingredient. In varying embodiments, the steroid or neurosteroid (e.g., allopregnanolone) is administered systemically (e.g., intramuscularly, intravenously, subcutaneously) at a dose in the range of about 0.25 mg/kg to about 15 mg/kg, e.g., about 0.25 mg/kg to about 15 mg/kg, e.g., about 0.25, 0.5, 1, 2, 3, 4, 5, 6, 7, 8, 9, 10, 11, 12, 13, 14, 15 mg/kg. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

In varying embodiments, the steroids or neurosteroids (e.g., allopregnanolone) are formulated for intrapulmonary administration. In various embodiments, the steroids or neurosteroids (e.g., allopregnanolone) are formulated for delivery via an inhaler.

In various embodiments, the steroids or neurosteroids (e.g., allopregnanolone) are nebulized. Methods and systems for intrapulmonary delivery of steroids or neurosteroids (e.g., allopregnanolone) are known in the art and find use. Illustrative systems for aerosol delivery of steroids or neurosteroids (e.g., allopregnanolone) by inhalation are described, e.g., in U.S. Pat. Nos. 5,497,763; 5,660,166; 7,060,255; and 7,540,286; and U.S. Patent Publication Nos. 2003/0032638; and 2006/0052428, each of which are hereby incorporated herein by reference in their entirety for all purposes. Preferably, the steroids or neurosteroids (e.g., allopregnanolone) are nebulized without the input of heat.

For administration of the nebulized and/or aerosolized steroids or neurosteroids (e.g., allopregnanolone), the size of the aerosol particulates can be within a range appropriate for intrapulmonary delivery, particularly delivery to the distal alveoli. In various embodiments, the aerosol particulates have a mass median aerodynamic diameter ("MMAD") of less than about 5 µm, 4 µm, 3 µm, for example, ranging from about 1 µm to about 3 µm, e.g., from about 2 µm to about 3 µm, e.g., ranging from about 0.01 µm to about 0.10 µm. Aerosols characterized by a MMAD ranging from about 1 µm to about 3 µm can deposit on alveoli walls through gravitational settling and can be absorbed into the systemic circulation, while aerosols characterized by a MMAD ranging from about 0.01 µm to 0.10 µm can also be deposited on the alveoli walls through diffusion. Aerosols characterized by a MMAD ranging from about 0.15 µm to about 1 µm are generally exhaled. Thus, in various embodiments, aerosol particulates can have a MMAD ranging from 0.01 µm to about 5 µm, for example, ranging from about 0.05 µm to about 3 µm, for example, ranging from about 1 µm to about 3 µm, for example, ranging from about 0.01 µm to about 0.1 µm. The nebulized and/or aerosolized steroids or neurosteroids (e.g., allopregnanolone) can be delivered to the distal alveoli, allowing for rapid absorption and efficacy.

In various embodiments, the steroids or neurosteroids (e.g., allopregnanolone) is formulated in a solution comprising excipients suitable for aerosolized intrapulmonary delivery. The solution can comprise one or more pharmaceutically acceptable carriers and/or excipients. Pharmaceutically acceptable refers to approved or approvable by a regulatory agency of the Federal or a state government or listed in the U.S Pharmacopoeia or other generally recognized pharmacopoeia for use in animals, and more particularly in humans. Preferably, the solution is buffered such that the solution is in a relatively neutral pH range, for example, a pH in the range of about 4 to 8, for example, a pH in the range of about 5-7. In some embodiments, the steroids or neurosteroids (e.g., allopregnanolone) is formulated in a buffered solution, for example, phosphate-buffered saline.

In various embodiments, the steroids or neurosteroids (e.g., allopregnanolone) is prepared as a concentrated aqueous solution. Ordinary metered dose liquid inhalers have poor efficiency for the delivery to the deep lung because the particle size is not sufficiently small (Kim et al., 1985 *Am Rev Resp Dis* 132:137-142; and Farr et al., 1995 Thorax 50:639-644). These systems are therefore used mostly for local delivery of drugs to the pulmonary airways. In addition, metered doses inhalers may not be able to deliver sufficient volumes of even a concentrated steroids or neurosteroids (e.g., allopregnanolone) solution to produce the desired rapid antiseizure effect. Accordingly, in various embodiments, a metered doses inhaler is not used for delivery of the steroids or neurosteroids (e.g., allopregnanolone). In one embodiment a nebulization system with the capability of delivering <5 µm particles (e.g., the PARI LC Star, which has a high efficiency, 78% respirable fraction 0.1-5 µm. see, e.g., pari.com) is used for intrapulmonary administration. Electronic nebulizers which employ a vibrating mesh or aperture plate to generate an aerosol with the required particle size can deliver sufficient quantities rapidly and find use (See, e.g., Knoch and Keller, 2005 *Expert Opin Drug Deliv* 2: 377-390). Also, custom-designed hand-held, electronic nebulizers can be made and find use.

Aerosolized delivery of steroids or neurosteroids (e.g., allopregnanolone) allows for reduced dosing to achieve desired efficacy, e.g., in comparison to intravenous or intranasal delivery. Appropriate dosing will depend on the size and health of the patient and can be readily determined by a trained clinician. Initial doses are low and then can be incrementally increased until the desired therapeutic effect is achieved with little or no adverse side effects. In various embodiments, the steroids or neurosteroids (e.g., allopregnanolone) are administered via the intrapulmonary route at a dose that is about 10%, 15%, 25%, 50% or 75% of established doses for their administration via other routes (e.g., via oral, intravenous or intranasal administration). In some embodiments, the steroids or neurosteroids (e.g., allopregnanolone) are administered via the intrapulmonary route at a dose in the range of about 0.05 mg/kg to about 1.0 mg/kg, for example, about 0.2 mg/kg to about 0.8 mg/kg, for example, about 0.05 mg/kg, 0.08 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, or 1.0 mg/kg. In some embodiments, the steroids or neurosteroids (e.g., allopregnanolone) are administered via the intrapulmonary route at a dose in the range of about 10 µg/kg to about 80 µg/kg, for example, about 20 µg/kg to about 60 µg/kg, for example, about 25 µg/kg to about 50 µg/kg, for example, about 10 µg/kg, 15 µg/kg, 20 µg/kg, 25 µg/kg, 30 µg/kg, 35 µg/kg, 40 µg/kg, 45 µg/kg, 50 µg/kg, 60 µg/kg, 70 µg/kg, or 80 µg/kg. In some embodiments, the steroids or neurosteroids (e.g., allopregnanolone) are administered via the intrapulmonary route at a dose in the range of about 0.3 µg/kg to about 3.0 µg/kg.

To prepare compositions, the steroid or neurosteroid (e.g., allopregnanolone) is mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the steroid or neurosteroid (e.g., allopregnanolone) in the selected carrier or vehicle. The effective concentration is sufficient for lessening or ameliorating at least one symptom of the disease, disorder, or condition treated and may be empirically determined.

Pharmaceutical carriers or vehicles suitable for administration of the steroids or neurosteroids (e.g., allopregnanolone) provided herein include any such carriers known to those skilled in the art to be suitable for the particular mode of administration (e.g., cyclodextrins). In addition, the active materials can also be mixed with other active materials that do not impair the desired action, or with materials that supplement the desired action, or have another action. The steroids or neurosteroids (e.g., allopregnanolone) may be formulated as the sole pharmaceutically active ingredient in the composition or may be combined with other active ingredients.

Where the steroids or neurosteroids (e.g., allopregnanolone) exhibit insufficient solubility, methods for solubilizing may be used. Such methods are known and include, but are not limited to, using cosolvents such as dimethylsulfoxide (DMSO), using surfactants such as Tween™, and dissolution in aqueous sodium bicarbonate. Derivatives of the steroids or neurosteroids (e.g., allopregnanolone), such as salts or prodrugs may also be used in formulating effective pharmaceutical compositions.

The concentration of the steroid or neurosteroid (e.g., allopregnanolone) is effective for delivery of an amount upon administration that lessens or ameliorates at least one symptom of the disorder for which the compound is administered and/or that is effective in a prophylactic context. Typically, the compositions are formulated for single dosage (e.g., daily) administration.

The steroids or neurosteroids (e.g., allopregnanolone) may be prepared with carriers that protect them against rapid elimination from the body, such as time-release formulations or coatings. Such carriers include controlled release formulations, such as, but not limited to, microencapsulated delivery systems. The active steroid or neurosteroid (e.g., allopregnanolone) is included in the pharmaceutically acceptable carrier in an amount sufficient to exert a therapeutically useful effect in the absence of undesirable side effects on the patient treated. The therapeutically effective concentration may be determined empirically by testing the steroids or neurosteroids (e.g., allopregnanolone) in known in vitro and in vivo model systems for the treated disorder. A therapeutically or prophylactically effective dose can be determined by first administering a low dose, and then incrementally increasing until a dose is reached that achieves the desired effect with minimal or no undesired side effects.

In various embodiments, the steroids or neurosteroids (e.g., allopregnanolone) and/or analogs thereof can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compounds. The containers are preferably adapted for the desired mode of administration, including, but not limited to depot products, pre-filled syringes, ampules, vials, and the like for parenteral administration The concentration and/or amount of steroid or neurosteroid (e.g., allopregnanolone) in the drug composition will depend on absorption, inactivation, and excretion rates of the steroid or neurosteroid (e.g., allopregnanolone), the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

5. Monitoring Efficacy

In various embodiments, administration of a steroid or neurosteroid (e.g., allopregnanolone) to a subject results in the prevention or mitigation of one or more symptoms of the disease condition being treated (e.g., traumatic brain injury, Alzheimer's disease, epilepsy, anxiety, fragile X syndrome, post-traumatic stress disorder, lysosomal storage disorders (Niemann-Pick type C disease), depression (including postpartum depression), premenstrual dysphoric disorder, alcohol craving, and smoking cessation). Symptoms of disease can be compared before and after administration of a steroid or neurosteroid (e.g., allopregnanolone) to the subject. Administration of the steroid or neurosteroid (e.g., allopregnanolone) to the subject is considered to be effective if the symptoms no longer occur after administration (e.g., seizures), or if the symptoms are reduced, alleviated and/or mitigated after administration.

In various embodiments, administration of a steroid or neurosteroid (e.g., allopregnanolone) to a subject results in the prevention of the occurrence of an impending seizure and/or the termination or abortion of a seizure in progress.

In various embodiments, efficacy can be monitored by the subject. For example, in a subject experiencing aura or receiving a warning from a seizure prediction device, the subject can self-administer a dose of the steroid or neurosteroid (e.g., allopregnanolone). If the steroid or neurosteroid (e.g., allopregnanolone) is administered in an efficacious amount, the sensation of aura should subside and/or the seizure prediction device should no longer predict the imminent occurrence of an impending seizure. If the sensation of aura does not subside and/or the seizure prediction device continues to predict an impending seizure, a second dose of steroid or neurosteroid (e.g., allopregnanolone) can be administered.

In other embodiments, the efficacy is monitored by a caregiver. For example, in a subject experiencing the onset of a seizure or in situations where a seizure has commenced, the subject may require administration of the steroid or neurosteroid (e.g., allopregnanolone) by a caregiver. If the steroid or neurosteroid (e.g., allopregnanolone) is administered in an efficacious amount, the seizure, along with the subject's symptoms of the seizure, should terminate or abort. If the seizure does not terminate, a second dose of the steroid or neurosteroid (e.g., allopregnanolone) can be administered.

EXAMPLES

The following examples are offered to illustrate, but not to limit the claimed invention.

Example 1

Anticonvulsant Activity of Intravenous and Intramuscular Allopregnanolone

Rationale:

Treatment of status epilepicus requires rapid administration of antiseizure agents, which are typically delivered either by the intravenous (i.v.) or intramuscular (i.m.) routes. Allopregnanolone (3α-hydroxy-5α-pregnan-20-one; 5α,3α-P), an endogenous progesterone-derived steroid that is a positive allosteric modulator of $GABA_A$ receptors, is a powerful antiseizure agent with potential in the treatment of status epilepticus. The objective of this study was to determine the dosing of allopregnanolone to protect against seizures when delivered i.v. and i.m.

Methods:

The mouse 6 Hz and pentylenetetrazol seizure models were used. Solutions of 5α,3α-P were made in 6% (0.5 and 1.5 mg/ml) sulfobutylether-β-cyclodextrin sodium salt (Captisol®) in 0.9% saline. The solutions were injected i.v. or i.m. (1, 2 and 30 min or 2 and 30 min, respectively) prior to administration of the 6 Hz electrical stimulus or PTZ (80 mg/kg, i.p.). In case of the PTZ model, animals were observed for 30 min and times to myoclonic jerks and clonic and tonic seizures were recorded. Anticonvulsant activity was assessed by the delay in onset of seizure signs. Allopregnanolone plasma levels in rats were determined by LC-MS.

Results:

5α,3α-P exhibited protective activity in the 6 Hz test 1-15 min after i.v. infusion (1.5 mg/kg) but was inactive at 30 min. In contrast, with i.m. administration (3 mg/kg) the onset of protective activity was slower (within 2 min) and lasted <2 h. At a dose of 0.1 mg/kg i.v. 5α,3α-P failed to significantly delay seizure onset in the PTZ model at all pretreatment times (1, 2 and 30 min) whereas a dose of 0.5 mg/kg administered 1 min before PTZ caused a marked delay for myoclonic jerks and clonic seizures and in 62.5% of animals prevented tonic seizures and mortality that invariably accompanies tonic seizures. When injected 2 min before PTZ 5α,3α-P (0.5 mg/kg) caused a similar increase in time to onset of seizures signs and prevented tonic seizures in 25% of animals.

5α,3α-P at a dose of 1.5 mg/kg completely prevented tonic seizures and mortality when injected i.v. 1 and 2 min before PTZ. When injected i.m. 2 min before PTZ, 0.25, 0.5 and 1.5 mg/kg 5α,3α-P protected 0%, 50% and 100%, respectively, of animals from tonic seizures. 5α,3α-P at the dose of 1.5 mg/kg i.m. provided significant protection against tonic seizures when injected 30 min before PTZ; the same dose injected i.v. 30 min before PTZ was inactive. In rats, an i.v. bolus dose of 0.5 and 1.0 mg/kg 5α,3α-P caused mean peak plasma levels (2 min) of 337 and 746 ng/ml, respectively; for both doses, the pooled mean two component halftimes were 2 and 22 min.

Conclusions:

Our results demonstrate that i.v. 5α,3α-P provides very rapid but transitory anticonvulsant activity. When injected i.m., 5α,3α-P acts comparably quickly and has a longer duration of action. Parenteral 5α,3α-P may be useful for the acute treatment of seizures.

Detailed Methods

Animals. Male NIH Swiss mice (22-30 g) served as subjects, and all procedures used in these studies were conducted in accordance with the University of California, Davis, Institutional Animal Care and Use Committee the Animal Care and Use policies in strict compliance with the *Guide for the Care and Use of Laboratory Animals* of the National Research Council (National Academy Press, Washington, D.C.; on the internet at nap.edu/readingroom/books/labrats/).

Test Substances and Drug Administration. Allopregnanolone (3α-hydroxy-5α-pregnan-20-one; 5α,3α-P) was synthesized by a SAFC Pharma Inc, Madison, Wis., USA and Captisol (sulfobutylether-beta-cyclodextrin sodium salt) was provided by Ligand Pharmaceuticals, Inc. La Jolla, Calif., USA. Solutions of 5α,3α-P were made in 6% (0.5 and 1.5 mg/ml) or 24% (6 mg/kg) sulfobutylether-β-cyclodextrin sodium salt (Captisol®) in 0.9% saline. The volumes used for all injections were 10-20 ml/kg of body weight. In order to establish time courses for protection by 5α,3α-P in the 6-Hz electrical-stimulation (32 mA, 3 s) model, 5α,3α-P (0.5-6 mg/kg) was administered intravenously (i.v.), intramuscularly (i.m.), subcutaneously (s.c.) or orally (p.o.) before electrical stimulation. In the PTZ seizure test, 5α,3α-P or vehicle were administered i.v. or i.m. 1, 2 or 30 min before PTZ.

Seizures Models

6-Hz Seizure Test (Kaminski, et al., *Epilepsia* (2004) 45:1-4): 3-s corneal stimulation (200-μs duration, 32-mA monopolar rectangular pulses at 6 Hz) was delivered by a constant-current device (ECT Unit 5780; Ugo Basile, Comerio, Italy). After the stimulation, the animals exhibited a "stunned" posture associated with rearing and automatic movements that lasted from 60 to 120 s in untreated animals. The experimental end point was protection against the seizure: an animal was considered to be protected if it resumed its normal exploratory behavior within 10 s of stimulation.

Pentylenetetrazol Seizure Test (Kokate, et al., *J Pharmacol Exp Ther* (1994) 270:1223-9): mice were injected intraperitoneally with PTZ (80 mg/kg) and were observed for a 30-min period. The time of onset of myoclonic jerks, clonus and tonic extension was recorded.

Surgery and Blood Collection. Male rats were implanted with indwelling jugular catheters as described (Baumann, et al., *J Neurosci*. (1998) 18: 9069-77). Animals were allowed to recover for at least one week. Experiments were carried out while the animal resided in its home cage. Rats received i.v. injection of vehicle or 5α,3α-P and serial blood samples were withdrawn into chilled tubes at 1, 2, 10,15, 30, 60 and 120 min after i.v. injection. 5α,3α-P and D4-5α,3α-P (internal standard) were extracted with SPE method from rat's plasma. The extracted 5α,3α-P and D4-5α,3α-P were quantified with ultra-performance liquid chromatography (UPLC)/Atmospheric-pressure chemical ionization (APCI)/tandem mass spectrometry (MS/MS).

Data Analysis. Results are expressed as mean±S.E.M.; the significance of the difference in the responses of treatment groups with respect to control is based on one-way analysis of variance (ANOVA) followed by specific post hoc comparisons using Dunnett's test. Differences were considered statistically significant when the probability of error was less than 0.05 ($p<0.05$).

Figure 2:
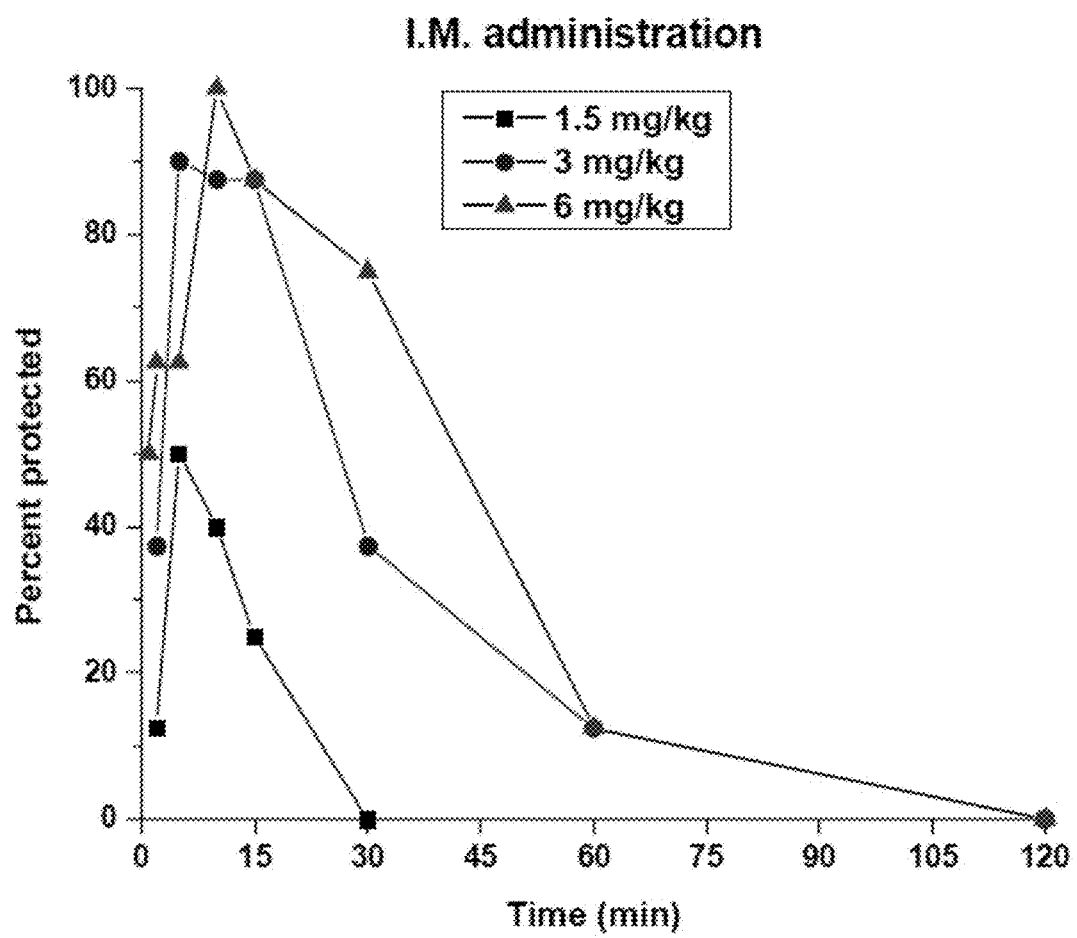
FIG. 2 illustrates a time course for protection by allopregnanolone (5α,3α-P) administered i.m. at a doses of 6, 3, 1.5 mg/kg in the 6-Hz electrical stimulation (32 mA, 3 s) model. The interval between the steroid injection and the electrical stimulus is plotted on the abscissa and the percentage of animals protected against seizures is plotted on the ordinate. Each point represents at least eight mice.
Figure 3:
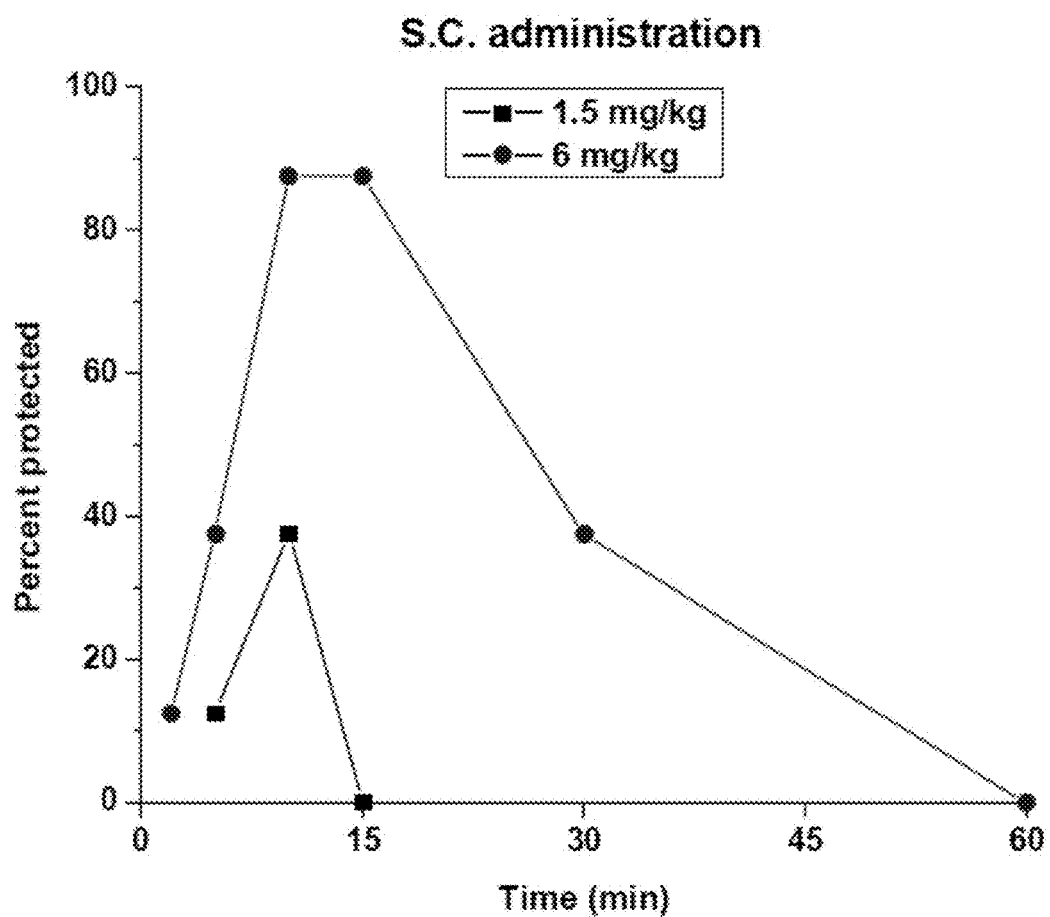
FIG. 3 illustrates a time course for protection by allopregnanolone (5α,3α-P) administered s.c. at a doses of 6 and 1.5 mg/kg in the 6-Hz electricalstimulation (32 mA, 3 s) model. The interval between the steroid injection and the electrical stimulus is plotted on the abscissa and the percentage of animals protected against seizures is plotted on the ordinate. Each point represents eight mice.
Figure 4:
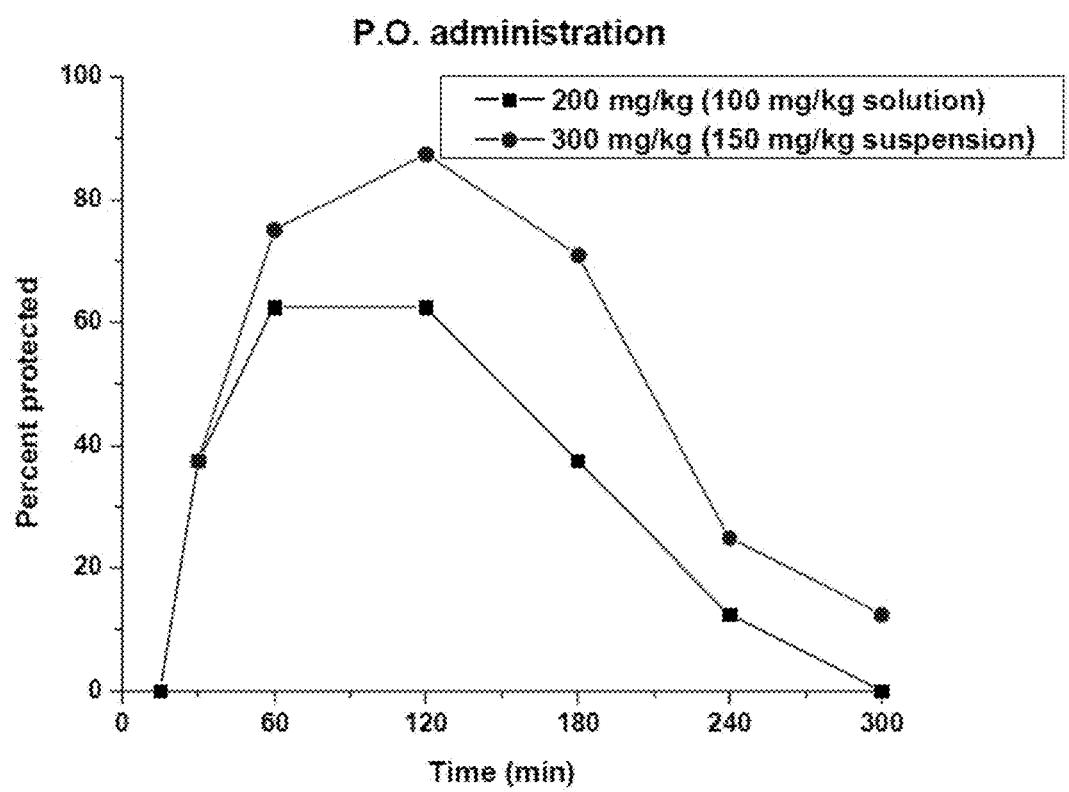
FIG. 4 illustrates a time course for protection by allopregnanolone (5α,3α-P) administered p.o. at a dose of 300 and 200 mg/kg (double volume of 150 mg/kg and 100 mg/kg suspended/diluted in Canola oil) in the 6-Hz electrical-stimulation (32 mA, 3 s) model. The interval between the steroid injection and the electrical stimulus is plotted on the abscissa and the percentage of animals protected against seizures is plotted on the ordinate. Each point represents at seven to eight mice.
Figure 5:
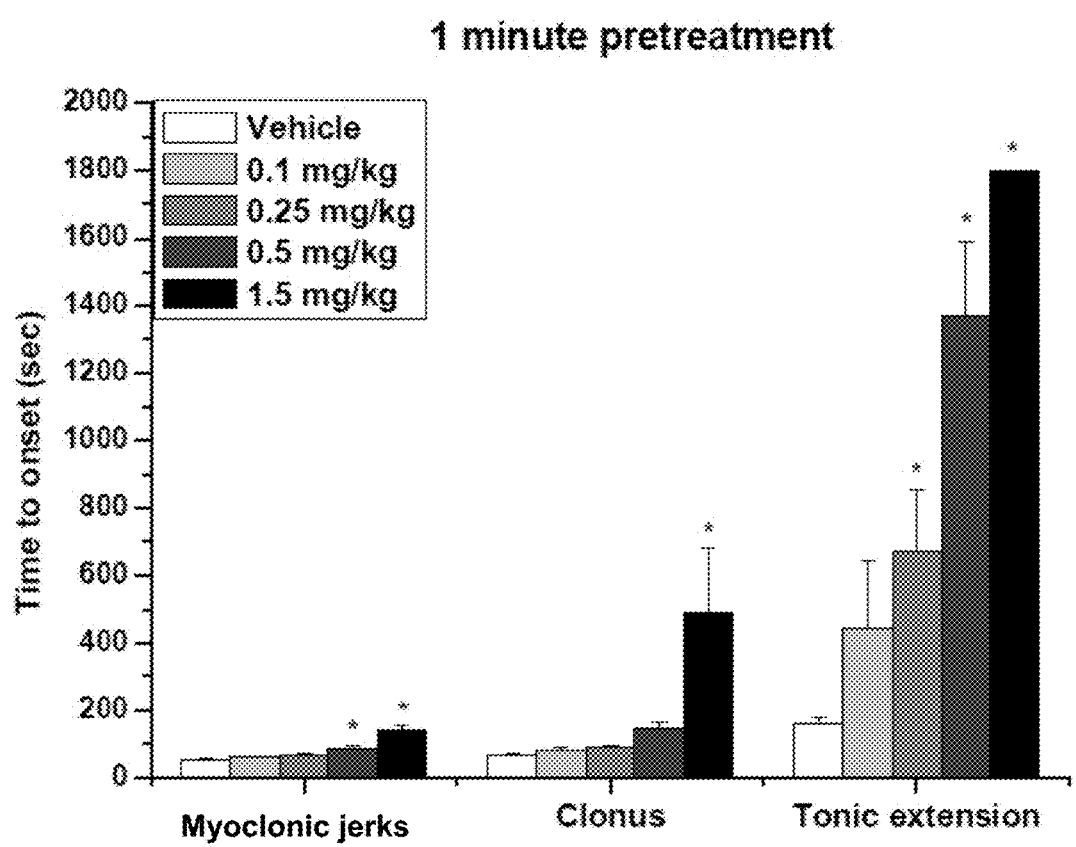
FIG. 5 illustrates the effect of i.v. administration of allopregnanolone (5α,3α-P) (0.1-1.5 mg/kg) on the onset of myoclonic jerk, generalized clonus, and tonic extension in response to PTZ (80 mg/kg, i.p.) injection in mice. 5α,3α-P was administered i.v. 1 min before PTZ injection. Bars indicate mean S.E.M. of values from eight mice. p<0.05 compared with vehicle control group (ANOVA followed by Dunnett's test).
Figure 6:
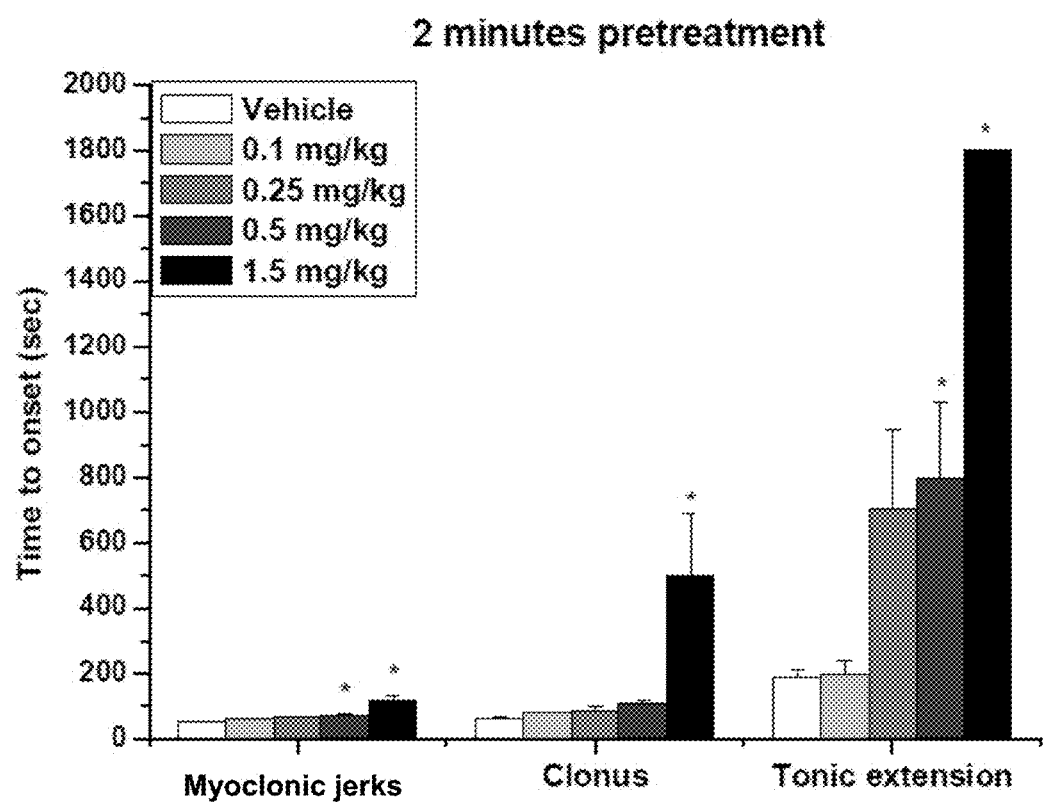
FIG. 6 illustrates the effect of i.v. administration of allopregnanolone (5α,3α-P) (0.1-1.5 mg/kg) on the onset of myoclonic jerk, generalized clonus, and tonic extension in response to PTZ (80 mg/kg, i.p.) injection in mice. 5α,3α-P was administered i.v. 2 min before PTZ injection. Bars indicate mean S.E.M. of values from eight mice. $p<0.05$ compared with vehicle control group (ANOVA followed by Dunnett's test).
Figure 7:
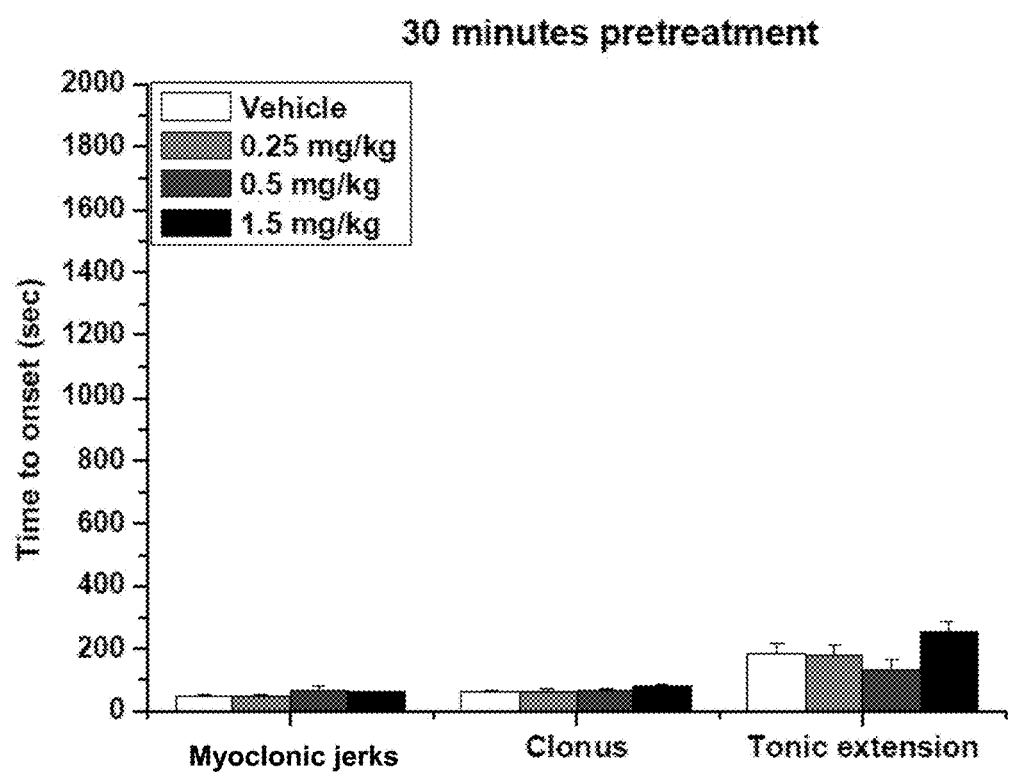
FIG. 7 illustrates the effect of i.v. administration of allopregnanolone (5α,3α-P) (0.25-1.5 mg/kg) on the onset of myoclonic jerk, generalized clonus, and tonic extension in response to PTZ (80 mg/kg, i.p.) injection in mice. 5α,3α-P was administered i.v. 30 min before PTZ injection. Bars indicate mean S.E.M. of values from eight mice. $p<0.05$ compared with vehicle control group (ANOVA followed by Dunnett's test).
Figure 8:
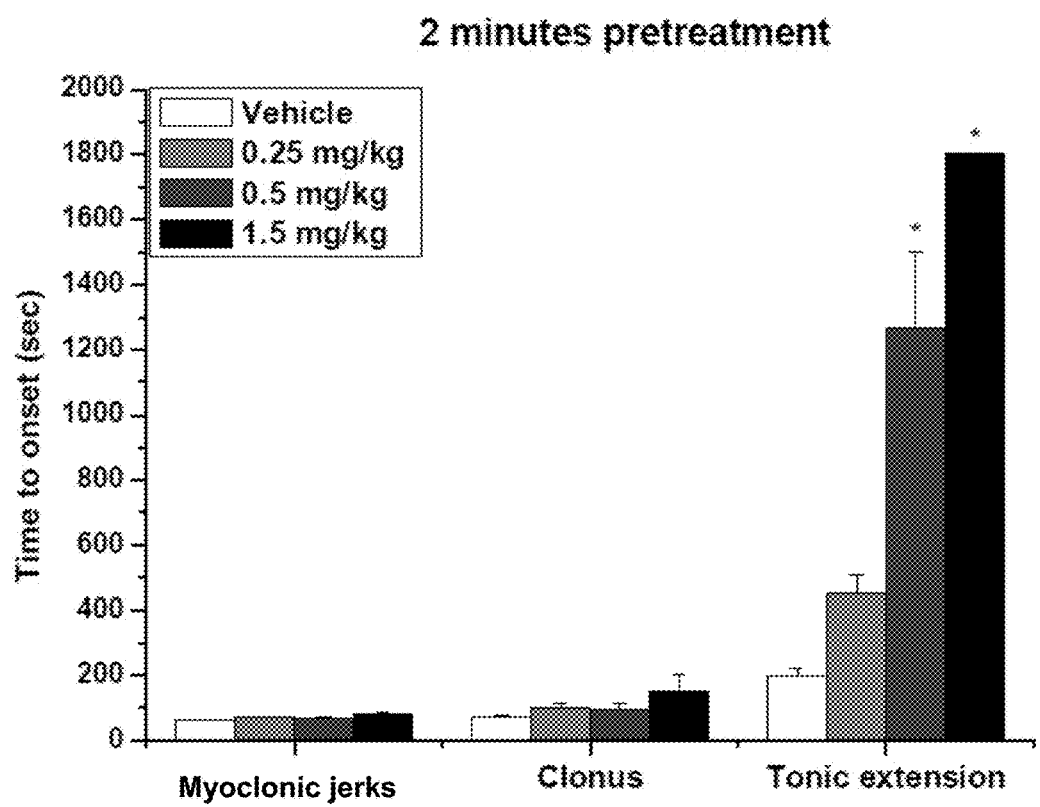
FIG. 8 illustrates the effect of i.m. administration of allopregnanolone (5α,3α-P) (0.25-1.5 mg/kg) on the onset of myoclonic jerk, generalized clonus, and tonic extension in response to PTZ (80 mg/kg, i.p.) injection in mice. 5α,3α-P was administered i.m. 2 min before PTZ injection. Bars indicate mean S.E.M. of values from at least seven mice. $p<0.05$ compared with vehicle control group (ANOVA followed by Dunnett's test).
Figure 9:
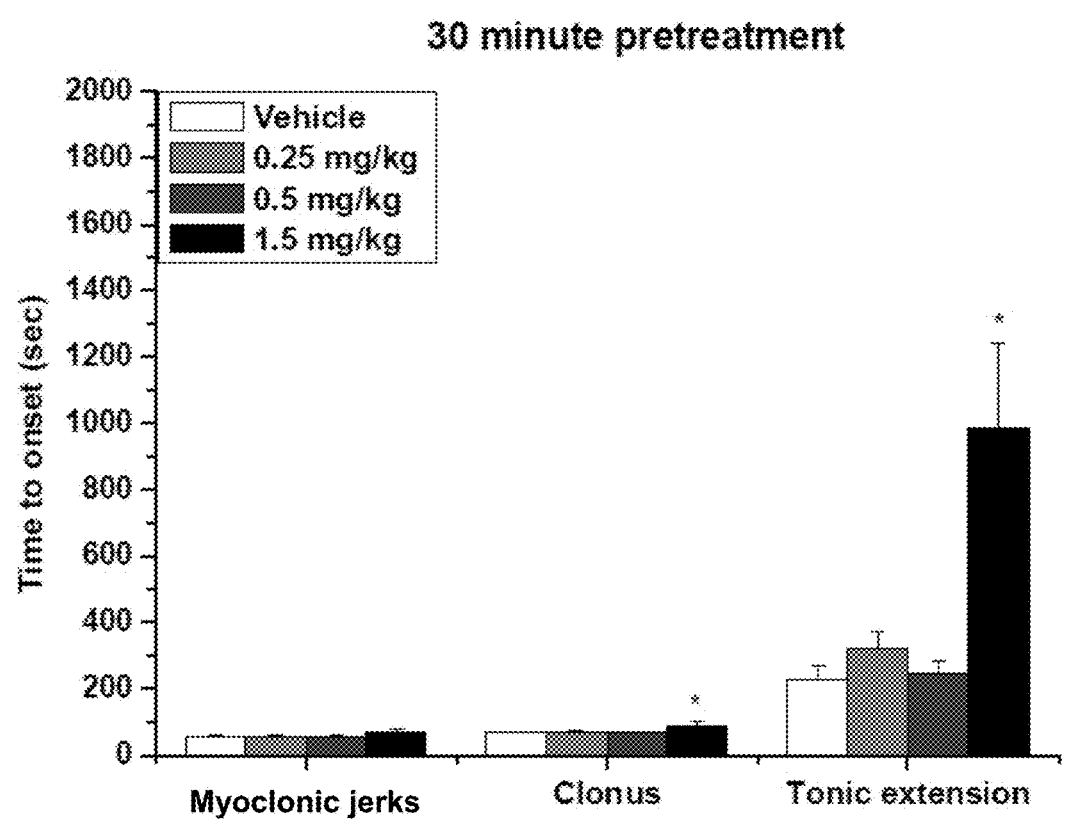
FIG. 9 illustrates the effect of i.m. administration of allopregnanolone (5α,3α-P) (0.25-1.5 mg/kg) on the onset of myoclonic jerk, generalized clonus, and tonic extension in response to PTZ (80 mg/kg, i.p.) injection in mice. 5α,3α-P was administered i.m. 30 min before PTZ injection. Bars indicate mean S.E.M. of values from eight mice. $p<0.05$ compared with vehicle control group (ANOVA followed by Dunnett's test).
Figure 10:
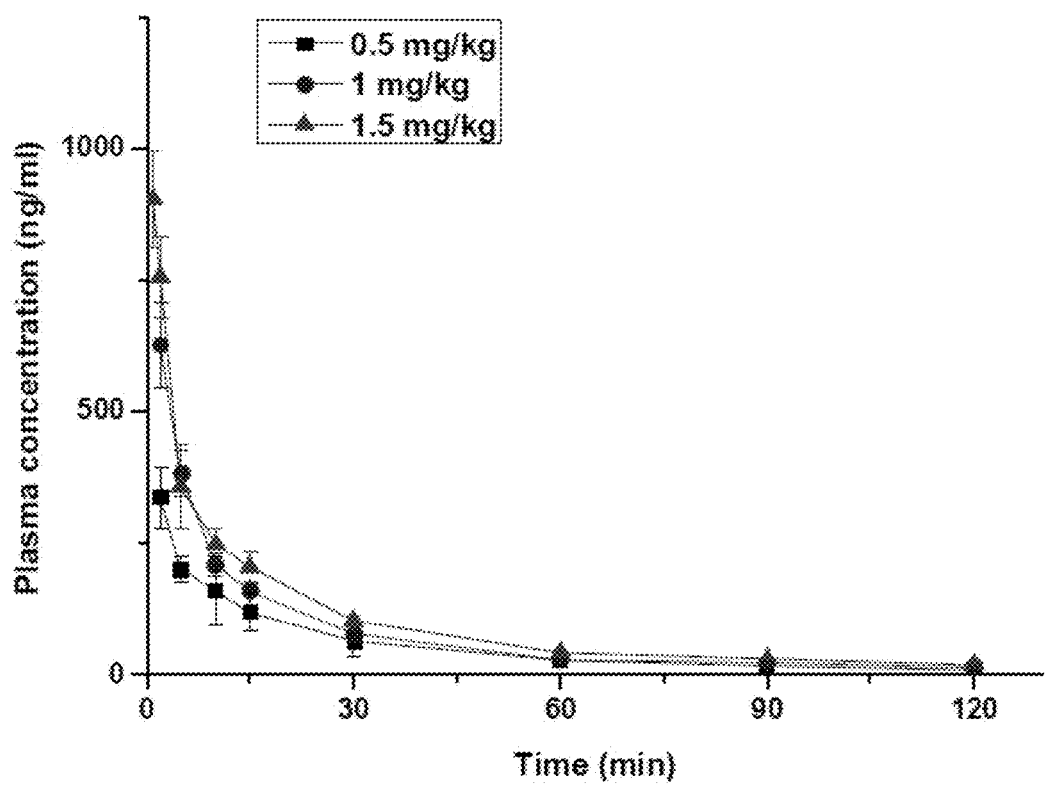
FIG. 10 illustrates a Time—concentration profile for plasma allopregnanolone (5α,3α-P) after single i.v. injection in rats. Rats bearing indwelling jugular catheters received single i.v. injection of 5α,3α-P or vehicle and serial blood samples were withdrawn at 1, 2, 10,15, 30, 60 and 120 min after injection. Plasma was assayed for 5α,3α-P by LC-MS. Each point represents at least 4 animals.

Results are shown in FIGS. 1-10. Our results demonstrate that i.v. 5α,3α-P provides very rapid but transitory anticonvulsant activity. When injected i.m., 5α,3α-P acts comparably quickly and has a longer duration of action. Low bioavailability of 5α,3α-P after oral administration prolongs the time of the peak effect and duration of action. Parenteral 5α,3α-P is useful for the acute treatment of seizures.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating post-partum depression in a subject in need thereof, comprising administering to the subject an effective amount of a composition comprising allopregnanolone and sulfobutylether-beta-cyclodextrin salt, wherein the composition is administered intravenously (i.v.).

2. The method of claim 1, wherein the subject is a human.

3. The method of claim 1, wherein the composition further comprises a buffer.

* * * * *